(12) United States Patent
Lyngstadaas et al.

(10) Patent No.: US 10,485,327 B2
(45) Date of Patent: Nov. 26, 2019

(54) BIO-RESORBABLE DEBRIDE OR IMPLANT CLEANING TOOL AND METHOD OF MANUFACTURING THE SAME

(71) Applicant: LABRIDA AS, Oslo (NO)

(72) Inventors: S. Petter Lyngstadaas, Nesoddtangen (NO); Johan Wohlfahrt, Oslo (NO)

(73) Assignee: LABRIDA AS, Oslo (NO)

( * ) Notice: Subject to any disclaimer, the term of this patent is extended or adjusted under 35 U.S.C. 154(b) by 510 days.

(21) Appl. No.: 14/357,055

(22) PCT Filed: Nov. 13, 2012

(86) PCT No.: PCT/EP2012/072487
§ 371 (c)(1),
(2) Date: May 8, 2014

(87) PCT Pub. No.: WO2013/072308
PCT Pub. Date: May 23, 2013

(65) Prior Publication Data
US 2014/0295378 A1 Oct. 2, 2014

Related U.S. Application Data

(60) Provisional application No. 61/559,171, filed on Nov. 14, 2011.

(30) Foreign Application Priority Data

Nov. 14, 2011 (SE) ........................................ 1151078

(51) Int. Cl.
*A61C 15/00* (2006.01)
*A46B 3/00* (2006.01)
(Continued)

(52) U.S. Cl.
CPC ................ *A46B 3/005* (2013.01); *A46B 5/02* (2013.01); *A46D 1/0215* (2013.01); *A61C 3/00* (2013.01);
(Continued)

(58) Field of Classification Search
CPC ........... A61C 15/00; A61C 17/00; A46B 5/02; A46B 3/005
(Continued)

(56) References Cited

U.S. PATENT DOCUMENTS 4,326,547 A * 4/1982 Verplank ................ A61C 15/02
132/321
4,395,943 A * 8/1983 Brandli .................... A46B 3/18
15/167.1
(Continued)

FOREIGN PATENT DOCUMENTS

JP 9-313252 A 12/1997
JP 2008-161271 A 7/2006
(Continued)

OTHER PUBLICATIONS

International-Type Search Report dated Sep. 7, 2012.
(Continued)

*Primary Examiner* — Nicholas D Lucchesi
(74) *Attorney, Agent, or Firm* — Cermak Nakajima & McGowan LLP; Malcolm K. McGowan

(57) ABSTRACT

The present invention is directed to a debridement and/or implant cleaning tool (1) in which the means for cleaning (4) is made of a biodegradable material. Thus, if parts of the means for cleaning (4) come loose during use, these will be degraded by natural processes in the body and will not remain in the body and cause negative body reactions.

21 Claims, 8 Drawing Sheets

(51) Int. Cl.

| | |
|---|---|
| *A46D 1/00* | (2006.01) |
| *A61C 3/00* | (2006.01) |
| *A61C 15/04* | (2006.01) |
| *A46B 5/02* | (2006.01) |
| *A61C 17/00* | (2006.01) |
| *A61C 8/00* | (2006.01) |
| *A61C 17/24* | (2006.01) |
| *A61F 2/30* | (2006.01) |

(52) U.S. Cl.
CPC ............ *A61C 15/00* (2013.01); *A61C 15/041* (2013.01); *A61C 17/00* (2013.01); *A61C 3/005* (2013.01); *A61C 8/0089* (2013.01); *A61C 17/24* (2013.01); *A61F 2002/30719* (2013.01); *F04C 2270/0421* (2013.01)

(58) Field of Classification Search
USPC ............................................ 433/216; 15/160
See application file for complete search history.

(56) References Cited

U.S. PATENT DOCUMENTS

| | | | |
|---|---|---|---|
| 5,040,977 A * | 8/1991 | Weissman | A61C 3/03 433/122 |
| 5,699,578 A * | 12/1997 | Dumler | A46B 3/18 132/321 |
| 5,760,118 A | 6/1998 | Sinclair et al. | |
| 5,940,923 A | 8/1999 | Gunning | |
| 6,179,617 B1 * | 1/2001 | Ruddle | A61C 3/005 433/102 |
| 6,345,406 B1 | 2/2002 | Dodd | |
| 7,722,613 B2 | 5/2010 | Sutterlin et al. | |
| 2002/0088473 A1 * | 7/2002 | Fonseca | A46D 1/00 132/218 |
| 2006/0174910 A1 * | 8/2006 | Coopersmith | A61C 17/16 132/321 |
| 2006/0243409 A1 * | 11/2006 | Fish | A61C 15/02 162/329 |
| 2008/0301893 A1 * | 12/2008 | Erskine-Smith | A46B 9/028 15/167.1 |
| 2010/0163073 A1 * | 7/2010 | Lyngstadaas | A46B 3/18 134/8 |
| 2010/0192320 A1 * | 8/2010 | Borsari | A46B 3/18 15/206 |
| 2012/0129129 A1 * | 5/2012 | Fehr | A46B 3/18 433/141 |
| 2013/0139850 A1 * | 6/2013 | Axelsson | A46B 3/00 134/6 |
| 2013/0327354 A1 * | 12/2013 | Akagi | A61C 3/005 134/6 |
| 2014/0000049 A1 | 1/2014 | Lyngstadaas et al. | |

FOREIGN PATENT DOCUMENTS

| | | |
|---|---|---|
| JP | 2009-515640 A | 4/2009 |
| JP | 2011-507646 A | 3/2011 |
| WO | WO2010/033208 A1 | 3/2010 |

OTHER PUBLICATIONS

International Search Report for PCT Patent App. No. PCT/EP2012/072487 dated Aug. 14, 2013.
International Preliminary Report on Patentability for PCT Patent App. No. PCT/EP2012/072487 dated Apr. 2, 2014.

* cited by examiner

BIO-RESORBABLE DEBRIDE OR IMPLANT CLEANING TOOL AND METHOD OF MANUFACTURING THE SAME

CROSS-REFERENCE TO RELATED APPLICATIONS

The present application is a national stage application under 35 USC 371 of International Application PCT/EP2012/072487, filed Nov. 13, 2012, which claims priority from Swedish application 1151078-1, filed Nov. 14, 2011, and U.S. Provisional application 61/559,171, filed Nov. 14, 2011; the contents of these priority applications are hereby incorporated by reference in their entirety.

TECHNICAL FIELD

This document relates to a tool for the in situ and/or ex situ cleaning and/or maintenance of medical implants and/or tissue surfaces, such as dental implants and dental tissues. In particular this document is discloses a debridement and/or implant cleaning tool of which at least one part is biodegradable and which may or can be designed to release substances that restrict microbial growth and/or modulate biological processes.

BACKGROUND ART

Medical implants are today frequently implanted into vertebrate animals, including humans, to replace anatomy and/or restore a function or appearance of the body.

Medical implants may be made of various materials depending on their intended use. Examples of materials include composite materials (mixed materials without chemical bond in between) and biodegradable materials that are absorbed by the body when they have fulfilled their tasks. Biodegradable materials are not only absorbed by the body but rather metabolized in the body and the end products completely secreted, excreted or exhaled from the body, e.g. as in the form of water and carbon dioxide. Silicon implants may be used to replace soft tissue parts. Stainless steel is a strong material often used when a high mechanical strength is necessary, such as for repairing fractures or replacing parts of joints. Polyethylene implants may be used for parts of joint replacement implants.

Also, many medical implants, such as e.g. dental implants, orthopedic implants and vascular stents, are metallic, i.e. they are made of a metal material. Examples of metal materials commonly utilized for constructing metallic medical implants are steel, titanium, zirconium, tantalum, niobium, hafnium and alloys thereof. In particular, titanium and titanium alloys have proved to be suitable to utilize for constructing medical implants. This is due to the fact that titanium is biocompatible, it has excellent corrosion resistance in body fluids, and it is light and strong.

Dental implants are utilized in dental restoration procedures in patients missing one or more teeth. A dental implant comprises a dental fixture, which is utilized as an artificial tooth root replacement. Thus, the dental fixture serves as a root for a new tooth. The dental fixture is typically screw-shaped, i.e. it has the threads of a screw. The implant is surgically implanted into the jawbone, where after the bone tissue grows around the fixture, optimally with the bone in direct contact with the implant surface. The process of integration of an implant into bone is called osseointegration when the bone grows directly in contact with the surface of the implanted fixture. By means of the osseointegration, a rigid, permanent installation of the implant is obtained.

Periodontal diseases are caused by bacteria and toxins in dental plaque, which is a sticky colourless film constantly forming on the surfaces of the teeth. These diseases are very common; it has been estimated that they affect as much as between 70-90% of the world population, and they are a major cause of tooth loss in people over 35 years of age. The most common forms of periodontal disease are gingivitis and periodontitis.

Periodontal disease is caused by bacterial deposits accumulating on tooth surfaces along the gingival margins and results in destruction of tooth-supporting tissues. The destruction of tooth-supporting tissues results in a deepening of the space (periodontal defect) between the root of the tooth and the gum tissue.

In patients with implants, a periodontitis-like condition may develop into a condition called peri-implantitis and is caused by the colonization of bacteria of the implants's surface. This condition is a new disease entity that has arrived with the more widespread use of dental implants. So far no predictable treatment strategy has been developed for healing of peri-implantitis, and no evidence based treatment regime is currently available. The infection may be caused by bacteria introduced during surgery or post-surgically by insufficient oral hygiene. Inflammation in the tissues surrounding the implant then causes loss of bone that ultimately may lead to loss of the implant. Patients with implants are also susceptible to developing a condition called peri-implant mucositis. This condition involves the presence of inflammation in the mucosa at an implant, but with no signs of loss of supporting bone in contrast to the observed bone loss in peri-implantitis patients.

Treatment of periodontal disease usually involves removing the bacterial deposits and dental calculus. This is commonly performed by manual scaling of the exposed root surface to remove bacterial deposits and dental calculus, including deposits in the gingival margin. However, full access for treating deeper periodontal pockets is difficult to achieve, resulting in remaining bacteria that may re-infect the tissue. Therefore, the treatment is often combined with surgical procedures to open the tooth pocket to expose the tooth. The roots are then mechanically freed from bacterial deposits and calculus but also granulation tissue and bacterial toxin removal. Alternative treatments also include debridement and rinsing of the subjacent affected tissue and local or systemic treatment with antibiotics and anti-inflammatory drugs.

Bacterial infections around implants are treated similarly with debridement of the exposed surfaces, and are of course not only a problem in the oral cavity but also in other parts of the body where implants are placed.

Further it is often advantageous or necessary to debride surgically exposed hard tissue surfaces. For example, debriding of surgically exposed hard tissue surfaces may be advantageous or necessary to perform before regenerative treatment, i.e. in order to prepare the hard tissue surfaces for regenerative treatment.

Rapid debridement treatment is important to ensure a better total treatment outcome. In addition, the total treatment outcome may also depend on the degree of damage caused onto the anatomical structure by the debridement tool used during the debridement procedure. Furthermore, the total treatment outcome may also depend on the amount of contaminating material residues that is left on the treated surface by the debridement tool. Contaminating material residues may trigger a foreign body response, toxic response or inflammation disproportionate to its beneficial effect.

In addition, the surface of implants and the surrounding tissue sometimes need cleaning after placement of the implant in the body. This is particularly important when an infection or contamination occurs. In these cases the surface of the ailing implant has to be cleaned from microbes and contaminants to stop the progression of the disease and potentially make re-integration of the implant possible. To maintain a stable treatment outcome and to prevent further disease progress, the implant surface must also be regularly cleaned both by the patient himself and by a dental professional in a clinic. If the implant surface is not sufficiently cleaned and maintained, it may lead to disease progression and eventually the loss of both the implant and the surrounding tissue, such as the jawbone.

Tools commonly used today for cleaning metallic implants are mostly designed for cleaning teeth and are relatively rigid and sharp in order to provide a thorough cleaning of the tooth root surfaces. Such cleaning tools may, for example, be made of stainless steel, titanium, hard metal alloys or hard polymers. These tools may not always be suitable for cleaning medical implants that often have a delicate surface structure that may be damaged when debrided with a rigid and sharp cleaning tool. Also, such cleaning tools may destroy the implant surface morphology and form surface damages in which bacteria may hide and adhere making surface decontamination difficult.

Also, the cleaning tools used for implant debridement today, leave contaminating material residues on the medical implant surface, or in the peri-implant tissue. Such material residues can cause a toxic reaction or a foreign body reaction and/or or other inflammatory reactions disproportionate to their beneficial effects, that may further exaggerate the peri-implant disease and thus potentially induce further loss of implant attachment.

In order to avoid the above-mentioned adverse events, a cleaning tool with a working part designed in a softer material may be utilized instead of the above-mentioned cleaning tools made of metals or hard plastics. The working part of said instruments may then be made of e.g. a plastic material, nylon or any other synthetic or natural fibers. One example of such a brush for cleaning a dental implant is disclosed in U.S. Pat. No. 6,345,406. However, the cleaning effect of such brushes on the medical implant surface is not as good as that of hard cleaning tools, i.e. it is easier to clean more efficiently and thoroughly by means of harder and sharper cleaning tools. In addition, in case such a brush is utilized for cleaning a medical implant surface, it is common that one or more soft bristles, or parts thereof, come loose from the tool and get stuck on the implant or in the surrounding tissue, e.g. mucosa, whereby toxic reactions or inflammation or infections often results.

Dental floss is a dental device for daily basis home care, dental and implant maintenance. Dental flosses or tapes are being used by patients to clean the spaces and remove plaque and deposits between the teeth or implants or between implants and teeth. The aim is to keep the gum or peri-implant mucosa margin clean and free of inflammation. Common floss materials are made of high tensile strength nondegradable organic polymers that rub off against the rough implant surface and thus inherently leaves significant amounts of contaminants locked into the surface structure. These contaminants are known to induce inflammatory responses that hampers the healing of the adjacent soft tissues and might actually provoke or exacerbate peri-implant disease.

As is evident from the above, the cleaning of implant surfaces and biological tissues are difficult and the methods available today are all suboptimal. In conclusion, there is a need for cleaning devices, which are strong enough to clean/debride well without damaging hard or soft tissue surfaces, and which does not leave contaminants on implants or in surrounding tissues that trigger toxic reactions, foreign body responses or other unfavorable inflammatory responses, and which may be utilized for relatively rapid cleaning of an implant or tissue surface.

Today, several implantable devices such as membranes, fixation plates, meshes, screws, tacks and sutures can be made of bioresorbable materials. However, so far no tools or instruments for medical use has been designed in biodegradable materials since there has been little interest for such devices, and the technology available has not been advanced enough to provide and manufacture biodegradable devices with the optimal combination of strength and degradability.

The object of the present invention is to overcome or at least mitigate some of the problems associated with the prior art.

SUMMARY

The arrival of peri-implantitis has resulted in a strong need for instruments specially designed for the debridement and/or maintenance cleaning of implant surfaces.

The present document discloses a debridement and/or implant cleaning tool wherein at least the part of the tool that comes in contact with the surface to be treated and is responsible for exerting the debriding and/or cleaning action is made of or consists of at least one biodegradable material. The tool is in particular a tool for the debridement and/or cleaning of a dental implant and/or dental hard tissue surface, in particular dental implants and the tissue surrounding such implants. In particular the debridement and/or implant cleaning tool is a tool for the debridement and/or cleaning of dental implants. As the part of the tool that comes in contact with the surface to be treated is made of a biodegradable material, if part(s) of this part of the tool would come loose during treatment, it is broken down in the body by natural processes, thereby minimizing the risk that loose parts remain in the body and cause negative reactions, such as inflammations, infections or allergic reactions. Further, the biodegradable materials do not negatively affect the surface(s) they are used for treating, e.g. they do not scratch or otherwise harm the surface(s). Thereby, the risk for negative reactions in the body are further decreased as e.g. scratches may form a point for attachment of bacteria and impurities.

The present invention thus relates to a new and inventive set of debridement and/or implant cleaning tools for debriding and/or cleaning implants and/or tissue surfaces where the working part (i.e. the part of the tool that comes into contact with the surface to be treated and that exerts the cleaning and/or debridement) of said tools are made of a bio-degradable material for improved outcome of mechanical debridement and maintenance procedures. The tools are typically single use dental implant and/or debridement instruments (hand-held or to be used in a rotating or oscillating hand piece or an ultrasonic device) or tools comprising or consisting of dental flosses or dental tapes made completely or partly of a biodegradable material primarily to be used for maintenance of dental implants affected by peri-implant mucositis or peri-implantitis (i.e inflammation and loss of attachment). The major difference between these instruments and other related instruments is the biodegradability which has its offspring in avoiding toxic reactions, foreign body reactions and/or adverse inflammatory reactions from non-biocompatible remnants from the working parts of the devices used, such as bristles or parts of bristles. The bio-degradable material may or may not contain chemical component(s) or biomolecule(s) that are released during use and/or degradation to restrict bacterial growth and/or to reduce proteolytic activity and/or to modulate inflammation and/or to stimulate soft tissue regeneration and bone formation.

Accordingly, the object of the present invention is to provide an improved medical or dental implant cleaning tool and/or a debridement tool for cleaning of an implant and/or tissue surface and/or debriding of such a surface(s).

The present document therefore discloses a debridement and/or implant cleaning tool 1 comprising an elongated base member 2 and means for cleaning 4 in a cleaning section 5 at a first end 6 of said base member 2; characterized in that said means for cleaning 4 is made of a biodegradable material. Such a tool 1 is mainly intended for use by medical personnel, such as oral surgeons, dentists or dental hygienists in a clinic. However, it may also be adapted for personal home care. The working end of the debridement and/or implant cleaning tool 1 therefore corresponds to the means for cleaning 4 in a cleaning section 5. The working end may be fully made of a biodegradable material, such as when the working end is formed by molding a biodegradable material, i.e. both the means for cleaning 4 and the part of the base member 2 in the cleaning section 5 are made of the same biodegradable material(s). However, it may also comprise the means for cleaning 4 made of a biodegradable material (s) attached to a base member 2 made of another material, such as when the debridement and/or implant cleaning tool 1 is in the form of a twisted-in-wire brush where the means for cleaning are inserted between at least two twisted wires 14, forming the base member 2, typically made of a metal material.

The means for cleaning 4 in the debridement and/or implant cleaning tool 1 may be in the form of bristles. Further, the base member 2 of the debridement and/or implant cleaning tool 1 may comprise or consist of a biodegradable material(s). The biodegradable material may be selected from the group consisting of polylactic acid (PLA, polylactide), polyglycolic acid (poly(glycolide); PGA), cross-linked alginates, trimethylene carbonate (TMC) and biodegradable polymers such as polymers of L-lactic acid, D-lactic acid and trimethylene carbonate polydioxanone (PDS, PDO), and poly(DL-lactide-co-L-lactide) (LDLPLA), poly(DL-lactide-co-glycolid) (DLPLG), poly (glycolide-co-trimethylene carbonate) (PGA-TMC), poly (L-lactide-co-glycolide) (LPLG), poly(e-caprolactone) (PCL), chitosan, collagen and any combination thereof. The biodegradable material may be chitosan, PLA or PGA. The biodegradable material may consist of LPLA, DPLA and PGA in a weight percentage ratio of about 85:10:5. The biodegradable material may consist of LPLA and DPLA in a weight percentage ratio of about 85:15. The biodegradable material may consist of LPLA and DPLA in a weight percentage ratio of about 58:42. The biodegradable material may consist of poly(eta-caprolactone) (PCL). The biodegradable material may consist of chitosan. In a debridement and/or implant cleaning tool, the means for cleaning 4 and said base member 2 may be made of the same biodegradable material(s).

The debridement and/or implant cleaning tool 1 may comprise an insert 3 for a rotating, oscillating or ultrasonic handpiece, such as a dental handpiece, at a second end 8 of the tool 1.

The means for cleaning 4 may be provided with a microbe growth inhibiting and/or microbe killing substance, such as an antibiotic or chlorhexidine.

The present document is also directed to a debridement and/or implant cleaning tool 1 which is connected to a motor-driven unit 17, such as a contra-angle hand piece such as a rotating, oscillating (horizontally and/or vertically) or ultrasonic hand piece, such as a dental hand piece.

In the debridement and/or implant cleaning tool 1 the means for cleaning (4) may be extended over the length of the cleaning section 5, so as to form a cylindrical, spherical, hour-glass shaped or tapered shape of the cleaning section 5.

In the debridement and/or implant cleaning tool 1 the means for cleaning (4) may be in the form of bristles. The bristles may have a length of 0.5-50 mm.

In the debridement and/or implant cleaning tool 1 the base member 2 may be formed of two or more wires 14 being twisted with each other and the means for cleaning 4 may be in the form of bristles inserted in between the twisted wires 14.

In the debridement and/or implant cleaning tool 1 at least part or all of the base member 2 between the insert 3 or the handle and the cleaning section 5 comprising the means for cleaning 4 may be covered by a protective coating 16. The base member 2 may formed of two or more metallic wires 14 being twisted with each other and having means for cleaning 4 in the form of bristles inserted in between the twisted wires 14, the protective coating 16 covering at least part of the twisted wires in the section between the insert 3 or the handle and the cleaning section 5.

The diameter of the cleaning section 5 in the debridement and/or implant cleaning tool 1 may be between about 0.5 and 5 mm. The cleaning section (5) may be about 5-12 mm long, such as 5-8 mm. The length of the debridement and/or implant cleaning tool 1, including both the base member 2 and the cleaning section 5 may be about 15-300 mm. The base member 2 may be hollow. The cleaning section 5 may be positioned in the immediate vicinity of the first end 6 of the base member 2. In the debridement and/or implant cleaning tool 1 there may also be a part of the base member 2 between the first end 6 and the cleaning section 5. Depending on the intended use of the debridement and/or implant cleaning tool 1, the length of the base member 2 between the cleaning section 5 and the second end 8 or an insert 3 may differ in order to enable the user to reach the areas to be cleaned and/or debrided.

This document also discloses a method for preparing such a debridement and/or implant cleaning tool 1 comprising the steps of mixing biodegradable substance(s) (i.e. the biodegradable material), such as the polymers and co-polymers disclosed herein, with a catalyst, and heating in suitable cast in an injection molding process. Such a method for preparing a debridement and/or implant cleaning tool 1 may comprise the steps of:

a) preparing a suspension of a biodegradable material(s) (i.e. a biodegradable substance(s)) in an aqueous solution;
b) pouring the suspension of step a) into a mould;
c) allowing the suspension to solidify during heating;
d) cooling to room temperature and removal of tool from molding cast.

Steps a) and b) are also suitable for preparing means for cleaning 4 in the form of bristles for a brush-like debridement and/or implant cleaning tool. The present document is therefore also directed to a method for producing means for cleaning 4 in the form of bristles, said method comprising the steps of:
a) extruding a melt or a solution of at least one biodegradable material into a monofilament;
b) bridling of monofilaments provided in step a) into a thread or string;
c) cutting the thread or string into means for cleaning 4 in the form of bristles.

In another aspect, the present document discloses an implant cleaning and/or debridement tool, wherein said tool comprises or consists of a dental floss or tape being made of or consisting of a biodegradable material(s). The present document is therefore also directed to a dental debridement and/or dental implant cleaning tool, wherein said dental debridement and/or dental implant cleaning tool comprises or consists of a dental floss or tape, characterized in that said dental floss or tape is made of or consists of a biodegradable material. The dental floss or dental tape may have a flat or round profile. The dental floss or dental tape may be made of a single strand of a chitosan filament or a spun bundle of chitosan filaments having a total diameter of 0.14-0.29 mm. The dental floss or dental tape may have a width of about 0.5-2 mm, and a thickness of about 0.1-0.5 mm. The biodegradable material in such a dental floss or dental tape may be selected from the group consisting of polylactic acid (PLA, polylactide), polyglycolic acid (poly(glycolide); PGA), cross-linked alginates, trimethylene carbonate (TMC) and biodegradable polymers such as polymers of L-lactic acid, D-lactic acid and trimethylene carbonate polydioxanone (PDS, PDO), and poly(DL-lactide-co-L-lactide) (LDLPLA), poly(DL-lactide-co-glycolid) (DLPLG), poly (glycolide-co-trimethylene carbonate) (PGA-TMC), poly (L-lactide-co-glycolide) (LPLG), poly(e-caprolactone) (PCL), chitosan, collagen and any combination thereof. The biodegradable material may be chitosan. The surface of the dental floss or dental tape may be provided with a microbe growth inhibiting and/or microbe killing substance, such as an antibiotic or chlorhexidine. The dental floss or dental tape may have stiffened polymer coated ends.

The present document is also directed to a method for producing a dental debridement and/or dental implant cleaning tool in the form of a dental floss or tape, said method comprising the steps of:
a) extruding of a melt or a solution of at least one biodegradable material as defined elsewhere herein into a monofilament
b) bridling of monofilaments provided in step a) into a thread or string to provide a dental floss or dental tape
c) optionally coating said dental floss or dental tape with more biodegradable polymer(s) and/or one or more active substance(s) and/or attaching stiffened polymer ends to said dental floss or tape.

Also disclosed herein are uses of the debridement and/or implant cleaning tool(s) for cleaning and/or debriding implants and/or hard and/or soft tissue surfaces and methods for treating conditions benefiting from cleaning and/or debridement using a tool 1. The present document is therefore also directed to the use of a debridement and/or implant cleaning tool disclosed herein for cleaning and/or debriding a medical implant surface, such as a dental implant surface, and/or a hard or soft tissue surface. The present document is also directed to the use of a debridement and/or implant cleaning tool disclosed herein for preparing an implant surface or a hard and/or soft tissue surface for regenerative treatment. The use may or may not involve surgery. The present document is also directed to the use of a debridement and/or implant cleaning tool disclosed herein for the debridement of surgically exposed implant surfaces, tooth root surfaces, furcation defects and/or bony defects before regenerative treatment. The present document is also directed to the use of a debridement and/or implant cleaning tool disclosed herein for the debridement of implant surfaces, tooth root surfaces, furcation defects and/or bony defects before regenerative treatment, which use does not involve surgery. The present document is also directed to the use of a debridement and/or implant cleaning tool disclosed herein for the prevention and or treatment of a condition selected from the group consisting of periimplantitis, periodontitis lesions, marginal periodontitis, apical periodontitis, furcation defects, apical granulomas and cysts, bone cysts, bone tumours, bone granulomas, bone cancers, extraction sockets, alveolitis sicca, cleaning of apicectomy defects, localized osteomyelitis, trauma induced defects, resection or revision of implants, resection or revision of fractures, and removal of temporary bone implants.

The present document also discloses an in vivo procedure for debriding and/or cleaning a tissue and/or a dental implant surface comprising the steps of:
a) surgically exposing the tissue surface to be treated;
b) removing inflamed soft tissue;
c) debriding and/or cleaning the surface(s) by means of the debridement and/or implant cleaning tool,
d) applying regenerative treatment as needed;
e) replacing soft tissue;
f) suturing for good primary closure and wound stability;
g) and allowing the wound to heal.

The present document also discloses a non-surgical in vivo procedure for debriding and/or cleaning a tissue and/or a dental implant surface comprising the steps of:
a) removing supragingival plaque and debris to gain direct access to a periimplant sulcus and/or periimplant pocket;
b) debriding and/or cleaning the surface(s) by means of the debridement and/or implant cleaning tool,
c) applying regenerative treatment as needed.

The present document also discloses an a method for debriding and/or cleaning a tissue or implant surface comprising the steps of placing a debridement and/or implant cleaning tool disclosed herein against the surface to be debrided and/or cleaned and moving said debridement and/or implant cleaning tool there over. Such a method may be used for the prevention and or treatment of a condition selected from the group consisting of periimplantitis, periodontitis lesions, marginal periodontitis, apical periodontitis, furcation defects, apical granulomas and cysts, bone cysts, bone tumours, bone granulomas, bone cancers, extraction sockets, alveolitis sicca, cleaning of apicectomy defects, localized osteomyelitis, trauma induced defects, resection or revision of implants, resection or revision of fractures, and removal of temporary bone implants.

Still other objects and features of the present invention will become apparent from the following detailed description considered in conjunction with the accompanying figures, and examples, and from the claims. It is to be understood, however, that the figures are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

Definitions

By "medical implant", "implant", medical prosthetic device" etc. is in the context of this document intended any structure used to support or restore a function of the body. Examples of such structures include, but are not limited to, dental implants, orthopaedic implants and vascular implants. In particular, these terms refers to structures having a supportive role in the body, thus being constructed of harder materials, such as metals or metal alloys.

The term "biodegradable material" or "biodegradable substance" in the context of the present disclosure means any natural or synthetic polymer, co-polymer or mixtures of two or more polymers that is biocompatible and resorbable for medical use that, when placed in the mammalian body are chemically, metabolically and/or enzymatically broken down to harmless constituents and metabolites (like sugars, weak organic acids, carbon dioxide and/or water) that are subsequently removed from the body through normal metabolism, excretion, secretion and/or exhalation. The biodegradable material(s) is therefore a biodegradable polymer(s).

By "debridement" is in the context of the present document intended removal of damaged, dead and/or infected tissue in order to improve healing of remaining tissue. The term "debridement" means cleaning of a hard tissue surface or an implant surface in order to remove, for example, biofilm, concretions, microbes, unwanted tissue, cells and cell residues, scar tissue, and/or necrotic tissue. Debridement may, for example, be performed in order to control local infections, inflammations, foreign body reactions, pathological conditions, degenerative processes (e.g. periodontitis, periimplantitis) and/or for preparing hard tissue surfaces for regenerative treatment.

By "cleaning", such as in the context of the term "implant cleaning", is in the context of the present document intended the removal of tissue, microorganisms, toxins, biofilm, organic components and/or mineral depositions (e.g. tartar and calculus) etc. from a surface, such as a medical implant surface, such as in particular a dental implant surface, or a soft or hard tissue surface. Cleaning thus refers to removing from a surface the bulk of contaminants leaving the surface clean enough (as opposed to aseptic or sterile) to allow normal biological processes to proceed without adverse effects or reactions against remaining contaminants.

By "biocompatible" and the like is in the context of the present document intended the quality of not having toxic or injurious effects on biological systems (see e.g. Dorland's medical dictionary).

By "made of" as used in context with the debridement and/or implant cleaning tool being "made of" a biodegradable material is meant that the main structural part of a specific part of the debridement and/or implant cleaning tool referred to is mainly composed or built up of a biodegradable material. By "mainly composed of" is meant that the part in question comprises at least 60%, 70%, 80%, 90%, 95, 96%, 97%, 98%, 99% or 100% biodegradable material. Any surface coatings are not included in these values, which only refers to the main structural part.

BRIEF DESCRIPTION OF DRAWINGS

FIG. 1 A depictures an exemplary debridement and/or implant cleaning tool tool 1 in the form of an injection molded brush. A tool 1 typically comprises an elongated base member 2 (a.ka. shaft), means for cleaning 4 positioned in a cleaning section 5 (a.k.a. working end) at a first end 6 of said base member 2, and an insert 3 for a motor-driven unit, such as a rotating, oscillating or ultrasonic dental hand-piece at a second end 8 of the tool 1. Instrument stem 7 comprises the insert 3 (or a handle) and the base member 2.

FIG. 6 A) A brush chitosan (i.e. a debridement and/or implant cleaning tool 1) with bristles (i.e. means for cleaning 4) made with working end (i.e. means for cleaning 4 in a cleaning section 5) of 2 mm in diameter and 8 mm in length with chitosan fibers 0.13 mm in diameter, double strand twisted in-wire of 0.3 mm medical grade stainless steel and a protective coating 16, here in the form of a mm nylon tube, covering the metal elongated base member 2, and tube inserted in to a stainless steel dental implant hand piece insert 3. B) the chitosan brush of A) inserted in motor-driven unit 17 in the form of a dental implant hand piece.

DETAILED DESCRIPTION

Figure 1A:
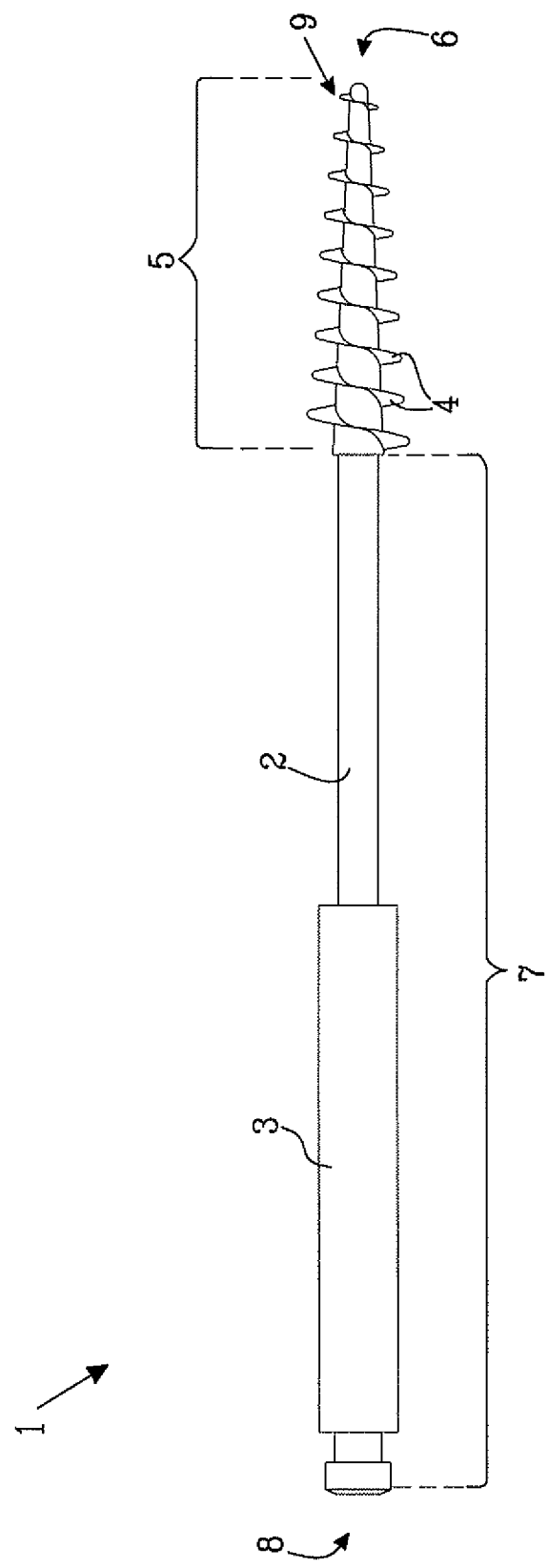
FIG. 1.
FIG. 1B depictures another exemplary design of a debridement and/or implant cleaning tool 1 having a bent base member 2 and another position of the irrigation canals 9.

In numerous situations today there is a need for debriding biological tissue surfaces and/or cleaning medical implant surfaces. However, currently available methods do not always result in a satisfactory result and/or have problems with damaging of tissues or delicate surfaces of medical implants. Further, the use of brush-like devices or dental flosses or tapes for debridement and/or cleaning involves the risk that bristles and the like or other parts of the brush come loose and are left in the body. This may lead to negative body reactions such as allergic reactions and may lead to an impaired healing.

This document therefore discloses a debridement and/or implant cleaning tool for the debridement and/or cleaning of tissue and implant surfaces, in particular hard tissue surfaces, and dental implant surfaces. In particular, the present debridement and/or implant cleaning tools are suitable for the debridement and/or cleaning of dental hard tissue surfaces, such as mineralized surfaces, and dental implant surfaces. Such debridement and/or cleaning may performed both in situ, i.e. on and around a structure, such as a tooth or dental implant, when such a structure is place in the body of a subject, and ex situ, i.e. when the structure is removed from the body, such as for debridement and/or cleaning before placing or replacing a structure in a body. In particular, the present document is directed to tools for use for the treatment and maintenance of dental implants and prosthesis, e.g. tools to be used in connection with the treatment and/or prevention of complications and/or disease associated with dental implants, such as peri-implantitis.

Due to its intended use, the debridement and/or implant cleaning tool of the present document may also be denoted a debridement tool, a dental debridement tool, an implant cleaning tool, a dental implant cleaning tool, a dental implant cleaning tool for the cleaning of dental implants, a dental implant cleaning tool for the cleaning of metallic dental implants, or a dental implant cleaning tool for the cleaning of metallic dental implants in the oral cavity.

The present document therefore discloses a debridement and/or implant cleaning tool, wherein at least the part of the tool that is responsible for the debridement and/or cleaning is made of one or more biodegradable material(s). This part of the tool may also consist of one or more biodegradable material(s).

This document in one aspect discloses a debridement and/or implant cleaning tool in the form of a debridement and/or implant cleaning tool 1 comprising an elongated base member 2 and means for cleaning 4 in a cleaning section 5 at a first end 6 of the base member 2, wherein the means for cleaning 4 is made of a biodegradable material. As the means for cleaning 4, or alternatively expressed, the cleaning arrangement 4, is made of a biodegradable material, if part(s) of it comes loose when the tool 1 is used, such part(s) are broken down by natural processes in a body and thus does not remain in the body. Thereby, the risk for negative body reactions against loose parts is decreased or diminished as they do not remain in a body for any longer time periods. This decreases the risk for allergic reactions, impaired wound healing, discomfort caused by a loose part etc.

Figure 1B:
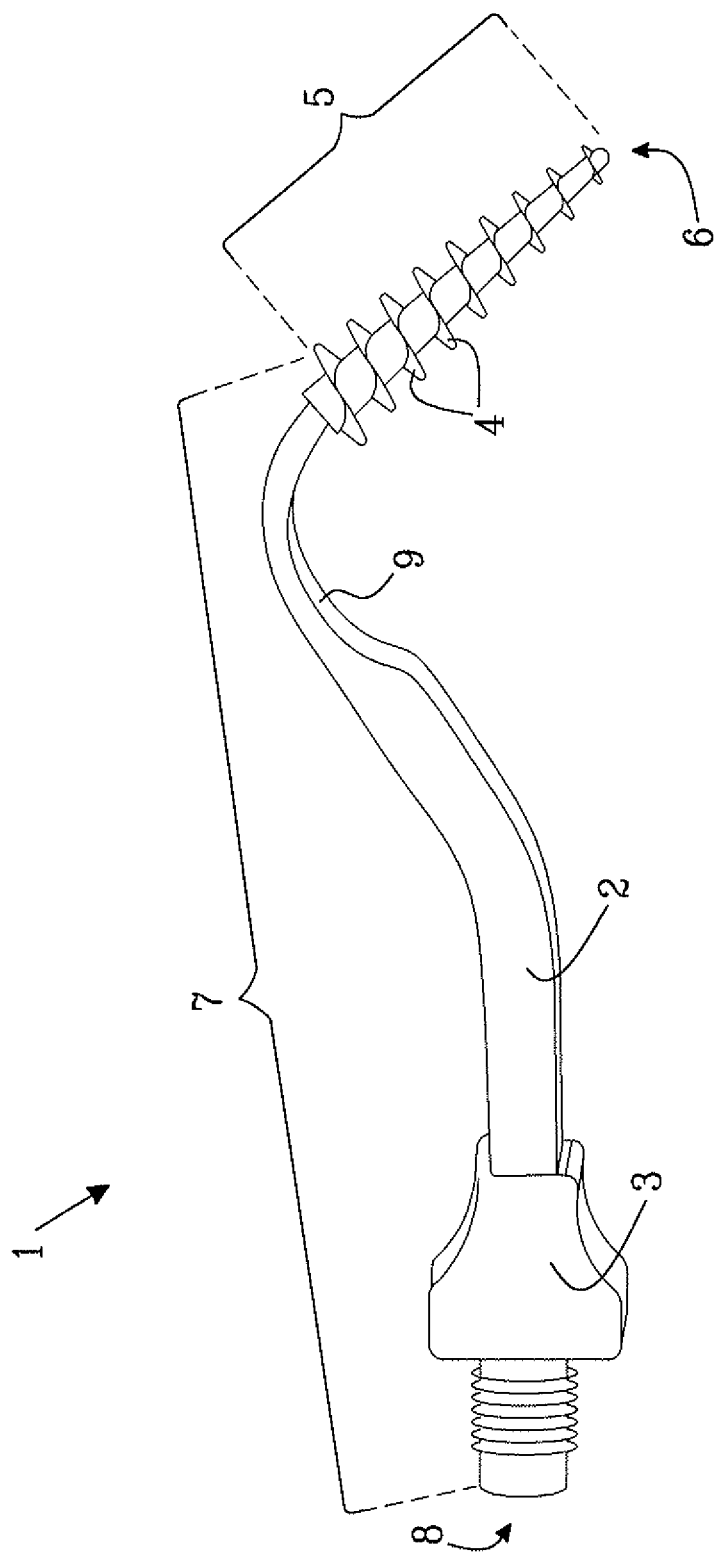
Figure 2:
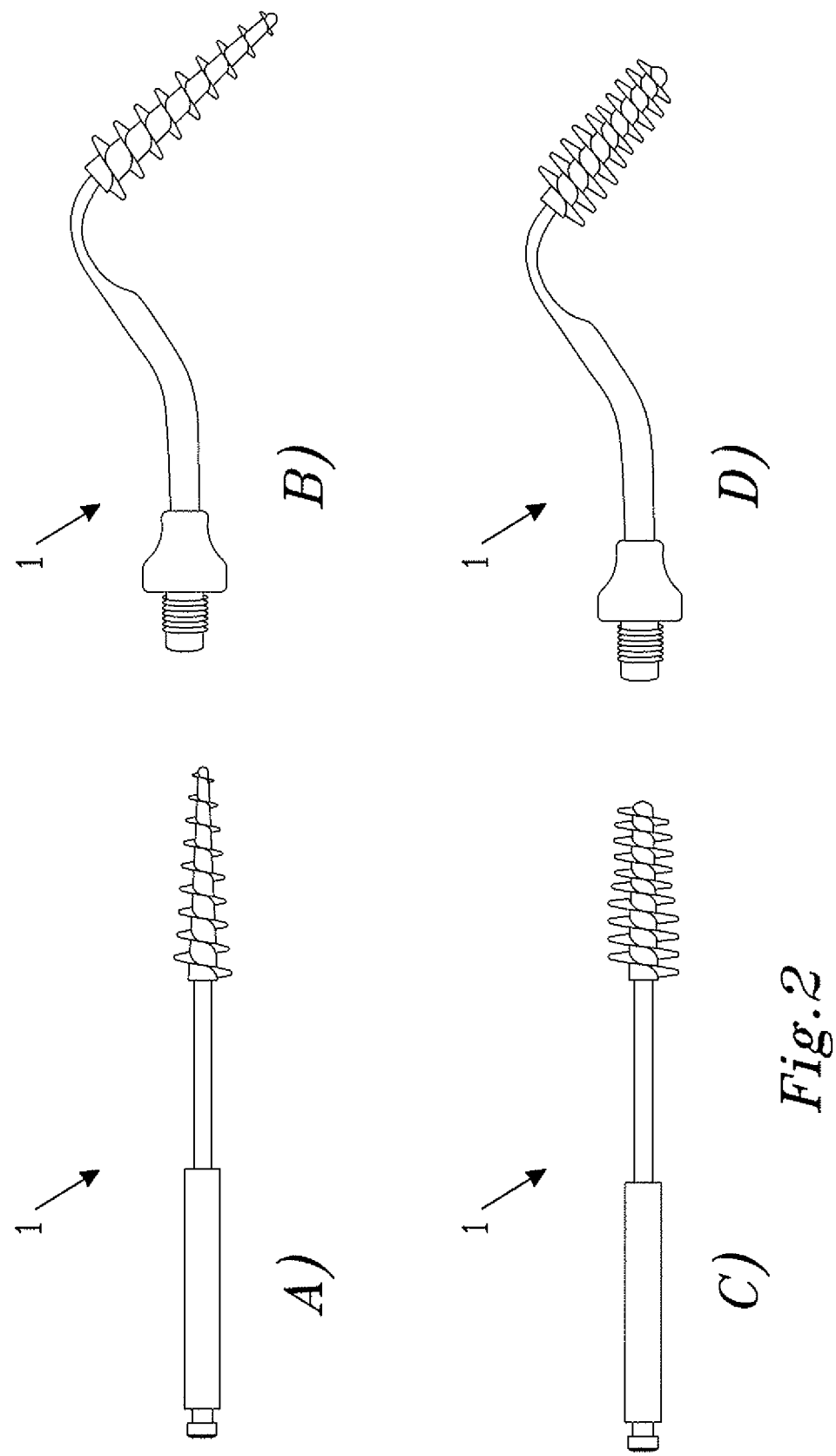
FIG. 2. Exemplary prototypes of the tool 1. The figures show schematically four different and exemplary embodiments (A-D) of the debridement and/or implant cleaning tool 1. All means for cleaning 4 are made of biodegradable material. A) Tapered brush with biodegradable pointed working end and with insert for regular rotating or oscillating dental handpiece. B) Ultrasonic insert with tapered brushtype biodegradable pointed working end, C) Straight brush with biodegradable blunt working end and with insert for regular rotating oscillating (horizontal and/or vertical) dental handpiece, D) Ultrasonic insert with straight brushtype biodegradable blunt working end.

Such a debridement and/or implant cleaning tool 1 may e.g. be designed as illustrated in FIG. 1 or FIGS. 2 A-D. These illustrations of the design of a tool 1 are only to be seen as exemplary and not limiting. Such a tool 1 typically at least comprises a base member 2 and means for cleaning 4. The means for cleaning 4 are positioned in a cleaning section 5 of the base member 2. The means for cleaning 4 are preferably extended over the length of the cleaning section 5, so as to form a cylindrical, spherical, hour-glass shaped or tapered (conical) shape of the cleaning section 5. These shapes are e.g. advantageous as they allow one to efficiently reach the surfaces that are to be cleaned and/or debrided. The typical peri-implant tissue defect is wide enough to allow cleaning with a cylindrical brush. A cylindrical brush is also the preferred shape as this allows for a uniform debridement of threaded surfaces, typically present on modern dental implants as well at undercuts and necks of abutments and prosthesis parts. Because of the sometimes complicated configuration of dental prosthesis fixed to the jaw with dental implants it is also necessary to have specialized cleaning devices that have shapes that can reach into crevices and occulted areas to remove concretions, biofilm etc. without having to expose the area through surgical intervention or disassembly of the prosthetic construct, which is not feasible for regular implant maintenance treatment. In FIG. 1A e.g., the means for cleaning 4 are positioned in the cleaning sections so that this adopts a tapered shape. Typically a tool 1, in addition to a base member 2 and a cleaning section 5 comprising the means for cleaning 4, comprises a handle suitable for manual use or an insert 3 for connection to a motor-driven unit 17, such as a rotating, oscillating (horizontally and/or vertically) or ultrasonic handpiece, such as a dental handpiece, at a second end 8 of the tool 1. The insert 3 may also be denoted a "connector", a "mandrel" or a "coupling". The use of a motor-driven unit 17 allows for the efficient debridement and/or cleaning of a surface due to the high frequency of rotation or oscillation and the ability to apply the necessary forces for debridement and/or cleaning as compared to using a handheld device. The use of a contra-angle handpiece also allow for more easy access to dental implants positioned in the back of the mouth where manual instrumentation is difficult or even impossible. This document is also directed to a debridement and/or implant cleaning tool 1 connected to such a motor-driven unit 17. The insert 3 or the handle may be made of the same material as the base member 2 (e.g. a biodegradable material) or be made of another material, such as metal or polyvinyl chloride (PVC). The insert 3 or the handle and base member 2, together denoted as the instrument stem 7 in FIG. 1, can e.g. be made of titanium, stainless steel or any type of polymer. The first end 6 can e.g. be tapered, blunt or straight. The choice of the shape of the first end 6 will e.g. be decided based on the surface to be debrided or cleaned, as different shapes will provide different abilities to reach different types of surfaces. A tapered end is advantageous for debriding and/or cleaning the narrowing space of the apical part of a peri-implant tissue pocket. A blunt end is advantageous for debriding or cleaning a surface that is exposed in a cup-shaped (blunt ended) defect or where the dental implant is substantially exposed into the oral cavity leaving the surface to be cleaned longer than the cleaning section 5 of the tool 1. A wide ended device is advantageous for cleaning occulted areas under undercuts and under prosthetic supraconstructions etc.

The base member 2 or part of it may be covered by a protective coating that protects the visible parts of the teeth or ceramic parts of the supraconstructions from abrasion and/or discolouration from contact with the base member 2 during debridement, in particular when the debridement and/or implant cleaning tool has a brush-like design. This protective coating 16 is placed on the base member 2 between the insert 3 or handle and the cleaning section 5 comprising the means for cleaning 4 (see e.g. FIGS. 6 and 7, wherein the protective coating is denoted 16). The protective coating is typically in the form of a tube covering at least part of the base member 2 between the insert 3 or handle and the cleaning section 5 comprising the means for cleaning 4, e.g. in the form of a plastic cap. It is important to note that the protective coating does not cover the means for cleaning 4 in the cleaning section 5. The protective coating typically is made of flexible nylon or PVDF (polyvinylidene fluoride) or any other similar material. The material is preferably white. Such a protective coating protects the surfaces that are cleaned and/or debrided and/or surrounding surfaces from discoloration and/or damage if they come in contact with the base member 2. During surgical debridement where the prosthetic part is removed and access to the implant surface is gained by surgery discoloration is not a major problem. However, when subgingival dental implant maintenance is performed nonsurgically and without removing of the prosthetic device (the ceramic teeth), discoloration and damage of prosthetic device surfaces is a problem. Because the prosthetic devices (the ceramic teeth) are wider in circumference that the dental implant and abutment to be cleaned, the base member 2 will inevitably come in contact with the white ceramic part of the prosthetic device (the ceramic teeth). The nature of the ceramic is such that the material of the base member 2 may rub off and discolour the ceramic surface where contact is made. This is particularly a problem when the base member 2 is made of a metallic material, such as when the debridement and/or implant cleaning tool 1 adopts a brush-like design with the base member 2 in the form of a twisted-in-wire configuration wherein the wires are made of a metal material as disclosed elsewhere herein and the means for cleaning 4 are in the form of bristles inserted between the twisted wires. To avoid this from happening, a strong but flexible polymer protective coating 16 may be applied to the base member 2 as disclosed above. Also, surprisingly, this protective coating 16 smoothens the action of a twisted-in-wire brush so that there is much less wobbling/vibration in the brush. This makes the brush easier to handle for the dentist/hygienist and the procedure more comfortable for the patient. Even more surprisingly, the polymer protective coating 16 completely prevents the involuntary slight up and down movement of the brush during operation imposed by the twisted base member 2 that act as a screw threads, further improving the operation and comfort of the debridement and/or implant cleaning tool 1. The effect is caused by the protective coating 16 providing a layer of less friction and which also may increase the diameter and covers the grooves of the twisted base member 2 to increase its clinical performance and comfort.

The present document is therefore also directed to a debridement and/or implant cleaning tool 1 wherein at least part or all of the base member 2 between the insert 3 or the handle and the cleaning section 5 comprising the means for cleaning 4 is covered by a protective coating 16. In particular, the present document is directed to a debridement and/or implant cleaning tool 1 wherein the base member 2 is formed of two or more metallic wires 14 being twisted with each other and having means for cleaning 4 in the form of bristles inserted in between the twisted wires, wherein at least part or all of the base member 2 between the insert 3 or the handle and the cleaning section 5 comprising the means for cleaning 4 is covered by a protective coating 16.

The debridement and/or implant cleaning tool 1 may be manufactured consisting only of the base member 2 and the means for cleaning 4 in a cleaning section 5.

When a debridement and/or implant cleaning tool 1 also comprises a handle, the handle may be a separate entity from the tool 1 or be an integral part of it. E.g. when the tool 1 is manufactured by molding the base member 2 and the means for cleaning 4 in one piece, the handle may be molded with the tool 1 at the same time, so that the resulting device comprises the tool 1 and the handle in one piece. One example of an advantage associated with producing the tool 1 or the tool 1 and the handle in one piece is an easier production method as the tool 1 is provided in one piece thus omitting the steps of having to produce all parts separately and then assemble them. Also, the resulting tool 1 is more robust and it does not comprise separately assembled parts. The production costs are also lowered.

The debridement and/or implant cleaning tool 1 may adopt a brush-like construction (such as e.g. illustrated in FIGS. 1-4), which may be either injection moulded or as a twisted in wire brush, wherein the means for cleaning 4 are in the form of bristles made of a biodegradable material. Therefore the debridement and/or implant cleaning tool 1 may comprise a base member 2 is formed of two or more wires being twisted with each other and means for cleaning 4 in the form of bristles inserted in between the twisted wires. However, it may as well adopt the construction of any other tool available for debriding biological tissue and/or for cleaning an implant such as a tooth pick like structure, dental floss or dental tape (see elsewhere herein). The means for cleaning 4 may therefore also be in the form of plates, threads etc. which are commonly used for (dental) debridement purposes or (dental) implant cleaning purposes, as long as the means for cleaning 4 are made of a biodegradable material. Exemplary constructions of a tool 1 in the form of a brush are illustrated in FIG. 1A.-B, FIG. 2 A-D, FIG. 3A-B, FIG. 4. An illustration of a debridement and/or implant cleaning tool in the form of a dental tape is illustrated in FIG. 5.

As mentioned above, the tool 1 may be formed by molding the base member 2 and the means for cleaning 4 in one piece. Alternatively, the means for cleaning 4 are typically welded onto a base member 2 or inserted in a twist stem configuration, wherein two or more wires are twisted with each other with the means for cleaning 4 inserted in between. The cleaning section 5 comprising the means for cleaning 4 may also be separately manufactured and then joined with a shaft corresponding to the part of the base member 2 which is not the cleaning section.

FIG. 2 A depicturs a tapered brush with biodegradable means for cleaning 4 in the form of bristles and with an insert 3 for regular rotating or oscillating dental handpiece. FIG. 2B depicturs a tool 1 with an ultrasonic insert 3 with tapered brushtype means for cleaning 4. FIG. 2C shows a straight brush with biodegradable means for cleaning 4 in the form of bristles and an insert 3 for regular rotating or oscillating (horizontal and/or vertical) dental handpiece, and FIG. 2D depicturs a tool 1 with an ultrasonic insert 3 with straight brushtype biodegradable means for cleaning 4.

The debridement and/or implant cleaning tool 1 may also comprise or consist of a dental floss or tape. The present document is therefore also directed to a dental debridement and/or dental implant cleaning tool, wherein said dental debridement and/or dental implant cleaning tool comprises or consists of a dental floss or tape, wherein said dental floss or tape is made of or consists of a biodegradable material. Such a dental floss or tape may be used by medical personnel in a clinic but may also be intended for use by the patient at home. The dental floss or tape of this document may either have a round or a flat profile. The dental floss or tape may have stiffened polymer coated ends for insertion in narrow spaces under dental bridge works and it may have a spongy surface texture for improved cleaning efficiency. A stiffened polymer coated end may be glued or melted on to the floss ends and are typically made of hard nylon. Such stiffened ends are designed to be pointed to allow more easy threading under dental prosthesis and or between dental implants and teeth, and/or to fit in holding tools or to fit the fingers of the patient for more easy use. The stiffened end may also be curved to help the floss thread back around the dental implant to assist the patient in retrieving both ends of the dental floss to be able to use it properly. The dental floss or tape may be designed as common dental flosses or tapes available and may e.g. comprise either of loose strands of various lengths (30 cm to 50 meter) or floss or tape attached to a plastic floss holder or floss wand of various already on the market existing types. The dental floss or tape may be either permanently connected (fused) to the floss holder or separate and attached to the holder before use. FIG. 5 depictures an exemplary dental tape attached to a holder.

The dental floss or tape is made of or consists of a biodegradable material. The properties and examples of such materials are disclosed elsewhere in this document. One example of a material suitable for use in a dental floss or tape is chitosan. Chitosan (poly acetyl glucose) is a deacetylated product of chitin, an abundant natural glucosamine polysaccharide found in nature and is also known as β-1,4-poly-D-glucosamine; poly-D-glucosamine; and poliglusam. Chitosan comprises predominantly polyglucosamine, and is generally prepared by the alkaline hydrolysis of chitin. The degree of deacetylation normally ranges from about 70 to about 98 percent. Chitosan has previously been used as a surface coating for dental flosses but in the present document, the dental floss as such is made of chitosan, i.e. its structure built up of chitosan.

The dental floss or dental tape may be made either of a single strand of a chitosan (mono)filament or a spun bundle of chitosan (mono)filaments typically having a total diameter of 0.14-0.29 mm. The filament(s) may be made in various lengths (such as 30 cm to 50 meter). In addition to the advantages obtained with using chitosan due to its biodegradable properties, chitosan may also have a hemostatic effect when used for treating surfaces.

When the dental floss or dental tape has a flat structure, the width of the floss or tape is typically about 0.5-2 mm, such as 0.5, 0.8, 1.0, 1.2, 1.4, 1.6, 1.8, or 2.0, and the thickness about 0.1-0.5 mm, such as 0.1, 0.2, 0.3, 0.4, or 0.5 mm.

One advantage with using chitosan as the biodegradable material in the debridement and/or implant cleaning tools disclosed herein is that it can easily be casted or extruded from a melt or solution. Further, debridement and/or implant cleaning tools made of chitosan have a physical strength which is favourable for their use for debriding and/or cleaning. Also, the metabolites formed when chitosan is degraded in a body are intrinsically anti-inflammatory. The degradation time of the chitosan is suitable (1-4 weeks) as such a degradation time is not so rapid that a massive release of acidic molecules resulting in a low local pH that may provoke tissue damage occurs, while still being short enough to not lead to not induce unwanted biological responses like allergic reactions, foreign body reactions and/or acute inflammatory responses. Chitosan is also a substance which is both bio-inert and biocompatible.

Advantages obtained with using such the dental floss or tape made of a biodegradable material(s) disclosed herein are the same as disclosed herein for the debridement and/or implant cleaning tool 1 having an elongated base member 2 and means for cleaning 4 in a cleaning section 5. Therefore, if part(s) of the dental floss or tape comes loose when used, such part(s) are broken down by natural processes in a body and thus does not remain in the body. Thereby, the risk for negative body reactions against loose parts is decreased or diminished as they do not remain in a body for any longer time periods. This decreases the risk for allergic reactions, impaired wound healing, discomfort caused by a loose part etc.

The present document is also directed to a method for producing a dental debridement and/or dental implant cleaning tool in the form of a dental floss or tape, said method comprising the steps of
  a) extruding a melt or a solution of at least one biodegradable material (i.e. biodegradable substance) as defined elsewhere herein into a monofilament
  b) bridling of monofilaments provided in step a) into a thread or string to provide a dental floss or dental tape
  c) optionally coating said dental floss or dental tape with more biodegradable polymer(s) and/or one or more active substance(s) and/or attaching stiffened polymer ends to said dental floss or tape, Steps a) and b) in the method for producing the dental floss or dental tape may also be used for producing bristles for use as means for cleaning 4 in a brush-like debridement and/or implant cleaning tool 1. The present document is therefore also directed to a method for producing means for cleaning 4 in the form of bristle comprising the steps of:
  a) extruding a melt or a solution of at least one biodegradable material as defined elsewhere herein into a monofilament
  b) bridling of monofilaments provided in step a) into a thread or string
  c) cutting the thread or string into means for cleaning 4 in the form of bristles.

As mentioned elsewhere herein, the surface of a dental debridement and/or dental implant cleaning tool in the form of a dental floss or tape may be provided with a microbe growth inhibiting and/or microbe killing substance, such as an antibiotic or chlorhexidine.

Chitosan filaments having suitable mechanical properties for a dental floss or tape or as cleaning means 4 in a tool 1 (such as bristles) as disclosed herein are disclosed in Table 1. For a dental floss or tape, spun chitosan fibers of USP 2/0 are typically used. For use as cleaning means 4 in a tool 1 comprising an elongated base member 2 and a cleaning section 5 (e.g. as depictured in FIGS. 1-4), chitosan filaments between USP 4/0 and 6/0 are typically used although chitosan filaments of thinner or larger diameters may also be used as cleaning means 4.

TABLE 1

Mechanical properties of chitosan fibers.

| Sample (USP size) | Diameter (mm) | Straight pulling (N) | Elongation at break (%) | N/mm² |
|---|---|---|---|---|
| 2/0 | 0.29 | 16.34 | 32.78 | 241.86 |
| 3/0 | 0.25 | 10.89 | 35.83 | 224.52 |
| 4/0 | 0.19 | 5.51 | 40.43 | 191.18 |
| 5/0 | 0.14 | 4.60 | 23.02 | 291.98 |
| 6/0 | 0.09 | 2.68 | 13.3 | 421.48 |

In the debridement and/or implant cleaning tool disclosed in this document at least the part of the tool that comes into contact with the surface(s) treated in order to provide the debriding and/or cleaning action is made of a biodegradable material, such as the means for cleaning 4 or the dental floss or dental tape. Suitable such biodegradable materials, e.g. for the means for cleaning 4 and optionally also other parts of a tool 1 (such as the base member 2 and/or the handle or insert 3) or the dental floss or dental tape include, but are not limited to, any natural or synthetic biodegradable polymer such as polylactic acid (PLA, polylactide), polyglycolic acid (poly(glycolide); PGA), cross-linked alginates, trimethylene carbonate (TMC) and biodegradable polymers such as polymers of L-lactic acid, D-lactic acid and trimethylene carbonate polydioxanone (PDS, PDO), poly(DL-lactide-co-L-lactide) (LDLPLA), poly(DL-lactide-co-glycolid) (DLPLG), poly(glycolide-co-trimethylene carbonate) (PGA-TMC), poly(L-lactide-co-glycolide) (LPLG), poly(e-caprolactone) (PCL), chitosan, collagen and any combination thereof. By poly(DL-lactide-co-L-lactide) (LDLPLA) is understood to mean co-polymers of L-lactic acid (LPLA) and DL-lactic acide (DLPLA). The biodegradable materials may also be denoted as bioresorbable materials. The means for cleaning 4 or the dental floss or tape may comprise one kind of biodegradable or a mixture of two or more biodegradable materials. Different parts of the means for cleaning 4 in the cleaning section 5 may also comprise different biodegradable materials and/or different mixtures of biodegradable materials. For example, the base member 2 may be constructed of polyurethane and the means for cleaning 4 of PLA or PGA or a combination thereof. Examples of preferred material for the working part of a biodegradable debridement and/or implant cleaning tool disclosed herein is the more simple molecules PGA or PLA or combinations thereof that degrade in vivo by hydrolysis into alpha-hydroxy acids that are further metabolized into carbon dioxide and water by the body.

The choice of biodegradable material may be used to adjust the strength of the debridement and/or implant cleaning tool. A stronger tool having more wear resistance is advantageous if the tool is only going to be used for debriding and/or cleaning. If active substances (for examples of such substances, see elsewhere herein) are to be deposited by means of the debridement and/or implant cleaning tool, a weaker design is more favourable as this allows for a "controlled" wear that deposits the active substance in an amount that is sufficient to obtain the desired effect. The person skilled in the art knows which polymer or combination of polymers will provide a suitable for a particular strength of the debridement and/or implant cleaning tool for the above purposes.

It will be appreciated that the copolymers may be linear or branched. The copolymers may be block copolymers, graft copolymers, alternating copolymers, periodic copolymers or statistical copolymers.

It will be appreciated that the polymers mentioned in this documents may be thermoplastics or thermosetting plastics.

One example of a biodegradable material is a biodegradable material which consists of LPLA, DPLA and PGA. The weight percentage ratio between the LPLA, DPLA and PGA may be about 85:10:5. Another example of a biodegradable material is a material consisting of LPLA and DPLA. The weight percentage ratio between the LPLA and DPLA may be about 85:15. A further example is a biodegradable material consisting of LPLA and DPLA. The weight percentage ratio between the LPLA and PGA may be about 58:42. Yet another example is a biodegradable material consisting of poly(eta-caprolactone) (PCL). Another example of a biodegradable material is chitosan.

For added strength, the biodegradable polymer(s) (biodegradable material(s)) can be mixed at different ratios to get a wide range of material properties. Combining several different biodegradable polymers into co-polymers enables a controlled degradation of the debridement and/or implant cleaning tool material and the possibility to load the material with active substances like antibiotics or growth factors or bioactive molecules that are released during the degradation of the material. Typically the biodegradable material used in a debridement and/or medical implant cleaning tool should have a strength that allows for efficient cleaning of several implant surfaces in the same patient without being worn down between implants, and at the same time have a degradation time in situ (i.e. in a body) of about 1 to 4 weeks.

A too rapid degradation could cause the massive release of acidic molecules resulting in a low local pH that may provoke tissue damage. On the other hand, a prolonged degradation time could induce unwanted biological responses like allergic reactions, foreign body reactions or acute inflammatory responses. The optimal combination of material strength and degradation time is crucial for an effective debridement as well as a favorable release profile of both degradation products and an active component(s).

The base member 2 may also be constructed by a biodegradable material, so that it comprises, is made of or consists of a biodegradable material. The biodegradable materials disclosed elsewhere in this document for the means for cleaning 4 are also suitable for use for the base member 2. The base member 2 may be constructed by the same biodegradable material(s) as the means for cleaning 4, or a different biodegradable material(s). For example, a tool 1 may comprise means for cleaning 4 and a base member 2 made of the same biodegradable material(s). The means for cleaning 4 and the base member 2 may be molded in one piece. Alternatively, the base member 2 may be made of a non-biodegradable material, such as a metallic, composite or plastic (e.g. polyurethane) material. Examples of metals suitable for the base member 2 includes, but are not limited to, steel, titanium or an alloy thereof, such as an alloy comprising titanium as base metal and at least one alloying component selected from the group consisting of: zirconium, tantalum, hafnium, niobium, aluminum, vanadium, molybdenum, chrome, cobalt, magnesium, iron, gold, silver, copper, mercury, tin and zinc, zirconium or an alloy thereof, tantalum or an alloy thereof, hafnium or an alloy thereof, niobium or an alloy thereof, or a chromium-vanadium alloy. Examples of plastic materials suitable for the base member 2 includes, but are not limited to nylon, polyethylene, vinyl, poly(methyl methacrylate) (PMA), polyvinyl chloride (PVC), polyvinylidene fluoride (PVDF), polytetrafluoroethylene (PTFE), or polyvinyl fluoride (PVF). The base member 2 may also comprise two or more different materials. These materials may either be intermixed with each other or different parts of the base member 2 may be constructed by different materials (which in themselves may comprise intermixed combinations of materials). The base member 2 may also be constructed of a material which is not biodegradable but coated with a biodegradable material.

The debridement and/or implant cleaning tool 1, including the means for cleaning 4, the base member 2, and any further parts, such as a handle or an insert 3, may also be fully made of biodegradable material(s), being the same or different for the different parts of the tool 1.

As mentioned above, an advantage of the use of a biodegradable material for the means for cleaning 4 and optionally the base member 2 or for making a dental floss or tape is that if these parts of the tool would come loose during use these parts are degraded by natural processes in the body. Thus such parts do not persist for longer periods in the body, and the risk for negative body reactions to the loose part, such as allergic reactions or the inclusion of the loose part in the body or its excretion through other body parts is decreased. Also, the use of the biodegradable materials allows simple manufacturing methods, such as molding to be used.

Figure 3:
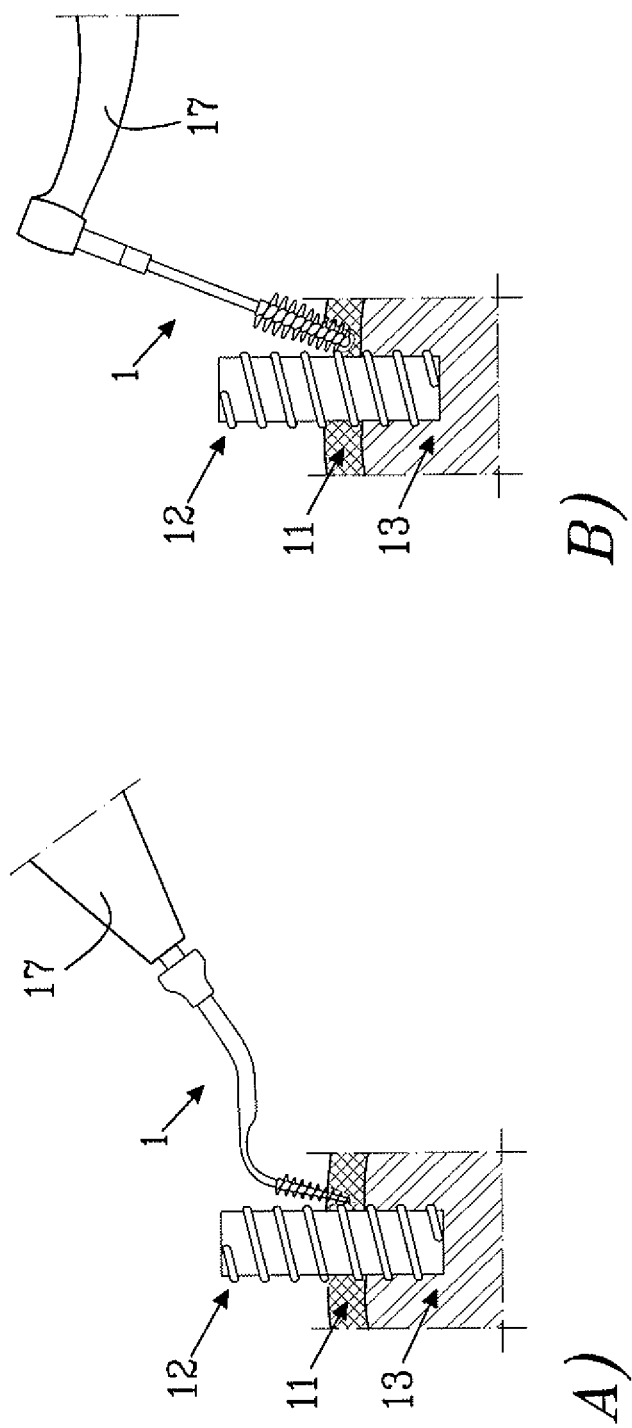
FIG. 3. Illustration of dental implant affected by peri-implantitis (i.e., bony attachment loss). Cross section of treatment of a peri-implant defect with the tool 1. Mucosa (gingiva) 11, dental implant 12, bone 13, peri-Implant bone defect A) Ultrasonic device 17 with attached resorbable device 1 (i.e. debridement and/or implant cleaning tool 1) B) Dental contra-angle handpiece 17 with attached resorbable device 1 (i.e. debridement and/or implant cleaning tool 1).

The biodegradable materials used in this document allow the construction of a debridement and/or implant cleaning tool 1 which is hard (stiff) enough to allow the effective cleaning of a surface, such as a biological tissue surface or the surface of an implant as depicted in FIG. 3. It is important that the means for cleaning 4, e.g. the bristles, are hard enough to allow for an efficient cleaning and/or debridement. Also, it may in some instances be important that the base member 2 has some degree of stiffness in order to be able to apply the pressure necessary to provide a cleaning action by the means for cleaning 4. However, it may in some instances be advantageous that the base member 2 is at least somewhat flexible if surfaces that are hard to reach are to be cleaned and/or debrided. The skilled person knows which biodegradable material(s) to select in order to The means for cleaning 4 of a debridement and/or implant cleaning tool 1 are thus hard enough to clean both hard and delicate biological tissue and/or implant surfaces. At the same time they do not have such hardness that they damage delicate surfaces, i.e. they do not essentially damage delicate surfaces. The same is true for a dental floss or tape made of such biodegradable material(s). Consequently, the risk of negatively affecting the surface structure of the biological tissue or medical implant is reduced when the tool 1 is utilized. In addition, when the damaging risk is reduced, the risk of formation of scratches constituting bacteria adherence sites is also reduced. Thus, the risk of re-infection in the tissue surrounding the implant, e.g. the gingival, is reduced too.

The cleaning section 5 and the base member 2 may be constructed in one piece, e.g. by molding the tool 1 in one piece. One example of a suitable technique for molding is injection molding. This provides e.g. an easy and cost-effective way of producing the tool 1 and also provides a tool wherein the parts that are in most contact with the body when used are made of a biodegradable material.

As mentioned above, the debridement and/or implant cleaning tool 1 may be constructed in the form of a brush (see FIG. 4 for an exemplary design) wherein the elongated base member 2 is formed of at least two wires 14 being twisted with each other, and wherein a plurality of bristles, making up the means for cleaning 4, are fixed between the twisted wires and extends away from the twisted wires, a so called twisted-in-wire design. The bristles are thus positioned in the cleaning section 5 at the first end 6 of the base member 2. 8 denotes the second end of the base member 2. Exemplary designs of such a tool, which are also suitable for a twisted-in-wire design of the tool 1 as disclosed herein, are given in WO 2009/083281. The tool 1 in the form of a twisted-in-wire brush may be attached to a handle or an insert 3 as disclosed elsewhere herein for manual or motor-driven use when connected to a motor-driven unit 17. The wires forming the base member 2 may e.g. be made of a biodegradable material disclosed elsewhere in this document or may be constituted by a metal material, such as titanium or titanium alloy, zirconium or zirconium alloy, aluminum or aluminum alloy, tantalum or tantalum alloy, hafnium or hafnium alloy, niobium or niobium alloy, aluminum or aluminum alloy, vanadium or vanadium alloy, molybdenum or molybdenum alloy, chrome or chrome alloy, cobalt or cobalt alloy, magnesium or magnesium alloy, iron or iron alloy, gold or gold alloy, silver or silver alloy, copper or copper alloy, mercury or mercury alloy, tin or tin alloy and zinc or zinc or zinc alloy, steel or a mixture of any of these.

The cleaning section 5 in a debridement and/or implant cleaning tool 1 may be positioned in the immediate vicinity of the first end 6 of the base member 2, i.e. with no part of the base member 2 between the first end and the cleaning section 5. Such a design may be advantageous when there is a short distance between the holder (hand piece) and the defect to be cleaned, i.e. if the prosthetic supraconstruction can be removed for maintenance. A shorter stem 7 will be less prone to wobbling or bending providing better control of the working part of the device. Alternatively, there may be a part of the base member 2 between the first end 6 and the cleaning section 5. Further, a longer part (such as 0.5-15 cm, 0.5-10 cm, 0.5-5 cm, or 1-5 cm, e.g. 0.5, 0.8, 1.0, 1.2, 1.5, 1.7, 2.0, 2.5, 3, 3.5, 4, 4.5, 5, 5.5, 6, 6.5, 7, 7.5, 8, 8.5, 10, 12, or 15 cm of the base member 2 towards the second end 8 of the tool 1 after the cleaning section 5, i.e. a longer stem 7, is needed to gain access to the areas to be cleaned when the prosthetic supraconstruction cannot be removed or the surface to be cleaned and/or debrided is not readily accessible. The cleaning section 5 with the means for cleaning may have different designs (such as round, cylindrical, hour-glass shaped or conical) especially adapted for different intended uses of the cleaning device, as described elsewhere in this document.

The debridement and/or implant cleaning tool 1 having an elongated base member 2 and means for cleaning 4 in a cleaning section 5 (e.g. a brush-like tool as depictured in FIGS. 1-4) is particularly suitable for the cleaning of dental implant surfaces, for e.g. removing biofilm, organic components and/or mineral depositions (e.g. tartar and calculus) from such dental implant surfaces, in particular metallic dental implants. The tissue surface surrounding the implant may also be cleaned in such a procedure. In particular such a tool 1 is suitable for cleaning dental implant surfaces of implants that are positioned in a body and exposed to the oral cavity. Such a tool 1 may be denoted a dental implant cleaning tool or a dental metallic implant cleaning tool. In order to be suitable for use for the cleaning of dental implants positioned in the oral cavity (i.e. in situ), the cleaning tool 1 has to be constructed so that it fits in the oral cavity and is able to reach the implant surface to be cleaned. Depending on the implant to be cleaned and where it is positioned in the oral cavity, the design of the cleaning section 5 with the means for cleaning 4 may be round, tapered, cylindrical or hour-glass shaped. As at least the means for cleaning 4 are made of a biodegradable material, if parts of the means for cleaning 4 would come lose during the cleaning of a dental implant in situ, such parts would remain on the implant surface where they will be degraded by the natural process in the body and the degradation products transported out in the oral cavity e.g. together with crevicular fluid without the loose parts being enclosed in living tissue.

When the means for cleaning 4 are in the form of bristles, the bristles may typically have a length of about 0.5-50 mm, such as about 0.5-5 mm, such as about 0.5, 1, 1.5, 2, 2.5, 3, 3.5, 4, 4.5 or 5 mm. The diameter of the bristles is typically 0.05-1 mm, such as about 0.05-0.5 mm, such as e.g. 0.05, 0.1, 0.2, 0.3, 0.4, 0.5, 0.6, 0.7, 0.8, 0.9 or 1 mm.

The means for cleaning 4 of the tool 1 may have a diameter that is constant over the length of the cleaning section 5 or a length that varies over the longitudinal length of the cleaning section 5. Independently on the design of the cleaning section 5, the diameter of the cleaning section 5 is typically between about 0.5 and 5 mm, such as about 0.5-3 mm, such as 0.5, 1, 1.5, 2, 2.5, 3, 3.5, 4, 4.5 or 5 mm. The diameter is typically 2.5-4.5 mm. The cleaning section 5 of the tool is typically about 5-12 mm long, such as about 5-8 mm, or such as about 5, 6, 7, 8, 9, 10, 11 or 12 mm. Typically, the cleaning section 5 with the means for cleaning 4 adopts a cylindrical, spherical, hour-glass or tapered shape.

The length of the tool 1, including both the base member 2 and the cleaning section 5, is typically about 15-300 mm, such as about 15-80 mm, such as 15-50 mm, such as about 15, 20, 50, 100, 150, 200, 250 or 300 mm.

It is also possible to provide the cleaning section 5 and/or the means for cleaning 4 with active substances to be released from a tool 1 when in use. The cleaning section 5 and/or means for cleaning 4 may e.g. be provided with a microbe growth inhibiting and/or microbe killing substance, such as an antibiotic or an antiseptic substance, e.g. silver, iodine or chlorhexidine. The substances may be present during the manufacturing of the tool 1, such as included in the materials that are used to manufacture the tool 1 (e.g. by being present in a suspension used for molding the tool 1). Such substance may also be added to a debridement and/or implant cleaning tool in the form of a dental floss or tape. Also, some biodegradable substances useful for the manufacture of a tool 1 are degraded to substances which have an acidic pH. For example, PLA is degraded to lactic acid and PGA to glycolic acid. As an acidic pH is disadvantageous for many bacteria, the degradation products in themselves provide an antibacterial effect. Thus, release products from material the tool 1 or the dental floss or tape is made of may in themselves have a beneficial effect, such as an antibacterial effect.

Further, the tool 1 or the dental floss or tape may be utilized together with a substance having a cleaning effect, such as an etching substance, e.g. hydrogen peroxide, a substance promoting healing of tissue or integration of implants, such as enamel matrix derived proteins and/or a microbe growth inhibiting and/or microbe killing substance, such as an antibiotic or chlorhexidine. Such substance(s) may be provided in a separate container with the tool 1 or the dental floss or tape in a kit of parts comprising a tool 1 or the dental floss or tape for application to the tool 1 or the dental floss or tape and/or the surface to be debrided and/or cleaned.

One advantage associated with the debridement and/or cleaning tool being made of a biodegradable material as disclosed herein, is that the biodegradable materials allows for a production where it is easy and comparatively cheap to produce a tool having the size, shape and/or choice of biodegradable material suitable for a specific application.

A tool 1 may be constructed as a straight tool. It may also adopt a bent structure as in exemplified in FIG. 2 C-F. The shape cleaning section 5 comprising the means for cleaning 4 is typically straight (conical), tapered, hour-glass shaped or spherical.

Although the dimensions exemplified in this document are those which will most often be suitable for the debridement of a biological tissue and/or cleaning of a medical implant, the exact size of the tool 1 or the dental floss or tape will of course depend on the intended use of it. For dental uses, the size of the tool is determined by the small space in the oral cavity in which the debridement and/or implant cleaning tool is to be used, which sets a natural limit to how large the dimensions of the tool can be. As mentioned above, one advantage with the present debridement and/or implant cleaning tool is that it is easy to adapt the size and shape of it for its intended use.

A tool 1 may have a shape wherein all means for cleaning 4 have essentially the same length, whereby the cleaning section 5 has a cylindrical shape.

In a tool 1, the means for cleaning 4 may have a varying length over, i.e. along, the longitudinal direction of the base member 2. The expression that "the means for cleaning 4 have a varying length over the longitudinal direction" is herein intended to mean that the length (i.e. the rise from the base member 2 in a direction vertical from the longitudinal direction of the base member 2) of at least part of the means for cleaning is different from other parts. The length of the means for cleaning 4 here increases successively in a direction from the part of the cleaning section 5 being closest to the first end 6 of the tool 1 (i.e. the cleaning section distal end) to the other end of the cleaning section 5 (i.e. the cleaning section proximal end), whereby the cleaning section 5 has a conical shape. This design of the tool 1 is particularly advantageous for the debridement and/or cleaning of deep and wide V-shaped pathological bone pockets. Such a conical shape of the tool 1 is also suited for debridement of a surgically exposed hard tissue surface, such as in treatment of, for example, wide bone defects, such as marginal periodontal defects and dehiscent defects. In this design, for example the cleaning section 5 may have a diameter that is about 0.8-1.2 mm in the end closest to the first end 6 and increasing to about 3.8-4.2 mm at the other end. The diameter of the cleaning section 5 may thus vary over its length from about 1 mm to about 4 mm.

The length of the means for cleaning 4 in the cleaning section 5 of a tool 1 may also vary along the longitudinal direction of the base member 2 so that the length of the means for cleaning 4 increases successively in a direction from the part of the cleaning section 5 being closest to the first end 6 of the tool 1 (i.e. a cleaning section distal end), to an intermediate position in the longitudinal direction of the cleaning section 5. Thereafter the length of the means for cleaning 4 decreases successively towards the other end of the cleaning section 5 (i.e. the cleaning section proximal end). The cleaning section has a diamond-like shape in a side view. This design of the tool 1 is particularly advantageous for the debridement and/or cleaning of narrow V-shaped pathological bone pockets.

Alternatively, the cleaning section 5 of the tool 1 may be ball-shaped. Then means for cleaning 4 has a varying length over the longitudinal direction of the cleaning section 5, whereby the length means for cleaning 4 increases successively in a direction from a first end of the cleaning section 5 to an intermediate position and thereafter decreases successively. The tool 1 thus has a substantially spherical shape. A tool 1 having a ball-shaped cleaning section 5 is particularly suited for debridement of a surgically exposed hard tissue surface, such as in the treatment of, for example, granulomas and apical periodontal defects.

An hour-glass shape of the cleaning section 5 of a debridement and/or implant cleaning tool 1 may be advantageous when one is to debride and/or clean surfaces in between two cylindrical or round dental implants placed close together. The hour-glass shape will then allow for a better and more efficient cleaning of both the adjacent surfaces simultaneously, covering a larger area of each implant in the process.

The above examples of shapes of the cleaning section 5 are only exemplary and may not be seen as limiting.

As is evident from the above, the size and shape of the debridement and/or implant cleaning tool, such as the tool 1 or the dental floss or tape, may be adapted to a defect anatomy, i.e. the size and shape of the debridement and/or implant cleaning tool, such as the tool 1 or the dental floss or tape, may be adapted such that it is suited for debriding of a particular type of surgically exposed hard tissue surface or the cleaning of a certain type of implant. For example, the cleaning section 5 of the tool 1 may be relatively long and narrow (i.e. the means for cleaning may have a relatively short length), whereby the tool 1 is suited for debridement of a surgically exposed hard tissue surface in treatment of, for example, vertical periodontics defects.

The tool 1 may or may not have an internal irrigation system i.e., the instrument stem 7 may or may not be hollow and with irrigation canals 9 at for example at the first end 6 of the base member 2 (see e.g. FIG. 1A) or other sites on the device (see e.g. FIG. 1B). The tool 1 may thus also be made hollow, i.e. the base member 2 may be made hollow in order to allow the distribution of a fluid through the tool 1, such as through the cleaning section 5, to a surface to be debrided and/or cleaned. Such a hollow tool 1 can be made with any design of the tool 1. If a twisted-in-wire construction is used, one of the wires may be made hollow. If the tool 1 is molded, the tool 1 may be molded with a hollow space in the base member 2. If the tool 1 is to be made hollow, the cleaning section 5 in such a design may comprise one or more, such as a plurality, of apertures through which fluid may be distributed. Alternatively or additionally, the first end 6 of the tool 1, i.e. the distal end of the cleaning section 5, may also comprise one or more apertures. Alternatively, the cleaning section distal end may be closed. Examples of fluids to be distributed by the tool 1 include, but are not limited to, water, saline, sterilized brine, hydrogen peroxide solution, antibiotic solution, weak acids (e.g. maleic acid, formic acid or another weak organic acid), diluted hydrogen fluoride (e.g. 0.005-0.1%). The fluid may be in order to irrigate for cooling, for removing debris, for dissolving concretions or mineral precipitations, for flushing the wound and the surface and for killing microbes during cleaning.

A tool 1 may be manufactured by molding, such as injection molding or pressfit molding. The techniques used are the standard molding techniques, but the starting suspensions are adjusted to the specific debridement and/or implant cleaning tool 1 to be formed. Factors affecting the choice of material(s), size and/or the shape of the tool 1 include for example the condition to be treated, the site of the body to be treated and the age and general condition of the subject. The means for cleaning 4 and the base member 2 may be molded separately and later assembled. Alternatively, the means for cleaning 4 and the base member 2 may be molded in one piece, optionally together with a handle or an insert 3. When the tool 1 is in the form of a twisted-in-wire construction, the means for cleaning 4, e.g. in the form of bristles, may be twisted in between the wires which form the base member 2.

The processing of a biodegradable debridement and/or implant cleaning tool 1 typically consist of either an injection molded working end fixed on a stem or carrier, or a biodegradable thread cut into bristles and fixed in a twisted in stem configuration. In the preferred process the working end material (i.e. the material of the means for cleaning 4 in the cleaning section 5) is made of predominantly PGA for strength with addition of other biodegradable polymers for increased elasticity and shear force strength and to reduce brittleness. The typical content of PGA is 50-98% whereas the added polymers can constitute between 45% and 1% of the bulk material. In addition a bioactive component can be added for release of the compound during the degradation of the working end material. The added bioactive component can constitute between 0.0001% and 4% of the bulk depending on the potency of the bioactive compound. The biodegradable material used for the means for cleaning 4 in the working end of the debridement and/or implant cleaning tool 1 is thermoplastic and can be melted and formed into fibers, rods and molded parts. Final parts can be extruded, injection molded, compression molded or solvent spun or cast, or even machined into final parts. In addition to the composition, the glass transition temperature and water content affects the physical characteristics of the final material. Here a glass transition temperature of above −10 degrees Celsius and preferably above 10 degrees Celsius is used. An even more preferred glass transition temperature would be above 37 degrees Celsius to ensure stability while being worked in the body. The maximum water content in the material during processing should be below 0.02% and preferably below 0.005% to avoid degradation during processing. Generally, production at the mildest conditions possible and with the rigorous exclusion of moisture are preferred.

A method for producing a debridement and/or implant cleaning tool 1 as described herein may e.g. comprise the steps of mixing the biodegradable substance(s) (i.e. biodegradable material(s)) disclosed elsewhere in this document with a catalyst, and heating in suitable cast in an injection molding process. The method may e.g. comprise the steps of a) preparing a suspension of a biodegradable substance(s) (biodegradable material(s)) in an aqueous solution b) pouring the suspension of step a) into a mould, c) allowing the suspension to solidify during heating, and d) cooling to room temperature and removal of tool from the mould. Thus, in the present method, an aqueous suspension comprising at least one biodegradable material is provided in step a). In step c), the suspension is allowed to solidify during heating thereby providing a casting. In step d), the cast is removed from the mould (i.e. the moulding cast), thereby providing a debridement and/or implant cleaning tool.

After processing, the biodegradable debridement and/or implant cleaning tool is quickly packaged in an airtight and moisture-proof bag, blister package or container under inert atmosphere or vacuum to avoid any moisture that can initiate the onset of hydrolytic degradation of the biodegradable material(s), e.g. the means for cleaning in the working end. The packaged debridement and/or implant cleaning tool should be stored at room temperature before being opened to avoid condensation prior to use. The final product should not be sterilized by autoclaving or dry heat because this will degrade or deform the device. Typically the instrument (the debridement and/or implant cleaning tool) is sterilized by gamma-irradiation, ethylene oxide (EtO) exposure, plasma etching or electron beam irradiation. Temperatures during sterilization must be kept below the glass transition temperature of the polymer to prevent the shape of the tool from changing during the process.

A debridement and/or implant cleaning tool, such as a debridement and/or implant cleaning tool 1 or a dental floss or tape, is useful for the debridement of a hard tissue surface and/or the cleaning of an implant, such as a dental implant in order to remove e.g. biofilm, concretions, microbes, unwanted tissue, cells and cell residues, scar tissue, and/or necrotic tissue.

The debridement/cleaning of a tissue surface or an implant may either be performed in vivo or in vitro. The latter may e.g, be used when an implant is removed from a body and needs to be cleaned before being put back. Further, lost teeth may need debridement before replacement in a body. An in vivo procedure involving use of the debridement and/or implant cleaning tool, e.g. the debridement and/or implant cleaning tool 1 or the dental floss or tape disclosed herein may, for example, involve the steps of:
  a) removing inflamed soft tissue;
  b) debriding and/or cleaning the surface(s) by means of the debridement and/or implant cleaning tool, i.e. the debridement and/or implant cleaning tool 1 or the dental floss or tape,
  c) applying regenerative treatment as needed;
  d) replacing soft tissue;
  e) suturing for good primary closure and wound stability;
  f) and allowing the wound to heal.

The present document is also directed to a non-surgical in vivo procedure for debriding and/or cleaning a tissue, such as a hard or soft tissue, and/or an implant surface, such as a dental implant surface, comprising the steps of:

a) removing supragingival plaque and debris to gain direct access to a periimplant sulcus and/or periimplant pocket;
b) debriding and/or cleaning the surface(s) by means of the debridement and/or implant cleaning tool,
c) applying regenerative treatment as needed.

This document therefore also discloses the use of a debridement and/or implant cleaning tool, such as a debridement and/or implant cleaning tool 1 or a dental floss or tape as disclosed herein, for cleaning and/or debriding a medical implant surface, such as a dental implant surface, and/or a hard tissue surface. Such a use of a debridement and/or implant cleaning tool for debriding and/or cleaning a tissue and/or implant surface may be surgical or non-surgical.

When the debridement and/or implant cleaning tool, such as the debridement and/or implant cleaning tool 1 or a dental floss or dental tape disclosed herein, is used for debriding and/or cleaning a surface, the debridement and/or implant cleaning tool 1 is placed against the surface to be cleaned and moved thereover, typically in a rotating or oscillating manner. When a rotational manner is used, typically a motor-driven unit 17 is used to effect such a movement. This document therefore also discloses a method for use of a debridement and/or implant cleaning tool 1 for any of the purposes specified herein wherein a debridement and/or implant cleaning tool 1 is placed against the surface to be cleaned and/or debrided and moved thereover. Such a method for debriding and/or cleaning a tissue or implant surface therefore comprises the steps of placing the debridement and/or implant cleaning tool 1 against the surface to be debrided and/or cleaned and moving said debridement and/or implant cleaning tool thereover. Such a method may be used for the prevention and or treatment of a condition selected from the group consisting of periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants (such as orthopaedic bone plates, retainers and screws). When the debridement and/or implant cleaning tool is in the form of a dental floss or tape, the floss or tape is used in the same manner as a regular dental floss or tape, i.e. it is placed next to the surface to be cleaned, e.g. inserted between an implant and an adjacent tooth or adjacent implant, and moved back-and-forth or up-and-down in order to debride and/or clean the surface. A dental floss or dental tape may be hand-held or attached to a hand held device to assist the user to clean the uppermost parts of the exposed dental implant necks and teeth. The present document also discloses the use of a debridement and/or implant cleaning tool as defined herein for the prevention and or treatment of a condition selected from the group consisting of periimplantitis, periodontitis lesions, marginal periodontitis, apical periodontitis, furcation defects, apical granulomas and cysts, bone cysts, bone tumours, bone granulomas, bone cancers, extraction sockets, alveolitis sicca, cleaning of apicectomy defects, localized osteomyelitis, trauma induced defects, resection or revision of implants, resection or revision of fractures, and removal of temporary bone implants. This use may or may not involve surgery.

This document is also directed to the use of a debridement and/or implant cleaning tool, such as a debridement and/or implant cleaning tool 1 or a dental floss or tape. The debridement and/or implant cleaning tool, such as a debridement and/or implant cleaning tool 1 or a dental floss or tape as disclosed herein, may be used for debriding a surface. The term "debridement" means cleaning of a hard tissue surface or an implant surface in order to remove, for example, biofilm, concretions, microbes, unwanted tissue, cells and cell residues, scar tissue, and/or necrotic tissue. Debridement may, for example, be performed in order to control local infections, inflammations, foreign body reactions, pathological conditions, degenerative processes (e.g. periodontitis, periimplantitis) and/or for preparing hard tissue surfaces for regenerative treatment. The debridement and/or implant cleaning tool, such as a debridement and/or implant cleaning tool 1 or a dental floss or tape, is particularly well suited for debridement of hard tissues such as bone, such as alveolar bone, cementum, teeth, dentin, enamel, cartilage and ligaments, even if the tool 1 may also be utilized for debridement and/or cleaning of soft tissue.

This document is therefore further directed to the use of a debridement and/or implant cleaning tool disclosed herein, such as a debridement and/or implant cleaning tool 1 or a dental floss or tape, for debriding an implant or a tissue surface, such as a dental implant or a hard tissue surface, such as bone or a dental surface. This document thus also discloses the use of a debridement and/or implant cleaning tool disclosed herein, such as a debridement and/or implant cleaning tool 1 or a dental floss or tape, for preparing an implant surface, such as a dental implant surface, or a hard and/or soft tissue surface for regenerative treatment. Further disclosed is a method for regenerative treatment comprising debriding an implant surface or a hard and/or soft tissue surface with a debridement and/or implant cleaning tool, such as a debridement and/or implant cleaning tool 1 or a dental floss or tape. Non-limiting examples of conditions, which may be associated with a treatment in which debridement and/or cleaning of a surgically exposed implant surface or a hard tissue surface may be performed by means of a debridement and/or implant cleaning tool, such as a debridement and/or implant cleaning tool 1 or a dental floss or tape, in order to prepare the surface for regenerative treatment, are: periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants (such as orthopaedic bone plates, retainers and screws). Furthermore, debridement of articular surfaces in joints affected by arthritis and debridement of such surfaces before regenerative treatment for cartilage and ligaments is instituted may also be performed by means of the debridement and/or implant cleaning tool, such as a debridement and/or implant cleaning tool 1 or a dental floss or tape. This document thus is also directed to the treatment of any of these conditions comprising debriding the surface with a debridement and/or implant cleaning tool as disclosed herein, such as a debridement and/or implant cleaning tool 1 or a dental floss or tape.

This document is also directed e.g. to the use a debridement and/or implant cleaning tool, such as a debridement and/or implant cleaning tool 1 or a dental floss or tape, for preparing a medical implant surface for regenerative treatment of a periimplant tissue defect. Further disclosed is also the use of a debridement and/or implant cleaning tool, such as a debridement and/or implant cleaning tool 1 or a dental floss or tape, in the treatment of a condition selected from the group of periimplantitis, infected implants, ailing implants, exposed implants, contaminated implants, restenosis of stents or any other conditions where implant structures needs debridement to recover normal function in the body.

In particular, the debridement and/or implant cleaning tool, such as a debridement and/or implant cleaning tool 1 or a dental floss or tape is an efficient tool for debridement of surgically exposed implant surfaces, tooth root surfaces, furcation defects and/or bony defects before regenerative treatment (i.e. by means of, for example Straumann® Emdogain, bone graft materials, autologous bone, membranes, etc.). The debridement and/or implant cleaning tool, such as a debridement and/or implant cleaning tool 1 or a dental floss or tape is especially effective for removing granulation tissue, and for removing concretions of calcified biofilms (plaques) and subgingival calcus. The present document is therefore also directed to the use of a debridement and/or implant cleaning tool as defined in herein, for debridement of implant surfaces, tooth root surfaces, furcation defects and/or bony defects before regenerative treatment. Such a use may or may not involve surgery.

The debridement and/or implant cleaning tool, such as a debridement and/or implant cleaning tool 1 or a dental floss or tape is well-suited for debridement of a surgically exposed implant and/or hard tissue surface, since the parts of the debridement and/or implant cleaning tool, such as a debridement and/or implant cleaning tool 1 or a dental floss or tape that contact the hard tissue surface in order to perform the debridement action, i.e. the means for cleaning 4 are hard enough to clean hard tissues surfaces well. At the same time the means for cleaning 4 efficiently debride the surface without imposing any damage to the anatomical structure, thus maintaining the outline of the original anatomy and/or implant surface morphology even after substantial instrumentation of the surface.

FIG. 3 is an exemplary illustration of the use of the debridement and/or implant cleaning tool in the form of a debridement and/or implant cleaning tool 1 for treatment of a peri-implant defect. The mucosa is denoted 11, the dental implant 12, and the bone 13. FIG. 3A shows an ultrasonic device with a debridement and/or implant cleaning tool 1 attached thereto. FIG. 3B shows a dental contra-angle handpiece with a debridement and/or implant cleaning tool 1 attached thereto.

As previously mentioned, if a biodegradable part of the debridement and/or implant cleaning tool, such as a debridement and/or implant cleaning tool 1 or a dental floss or tape, would come loose during use, and/or remain on the surface after debridement and/or cleaning, in the body, this piece will be degraded by natural processes in the body and will thus not persist in the body for any longer time periods. One effect of this is e.g. that the inflammation risk due to a loosened piece from the debridement and/or implant cleaning tool, such as a debridement and/or implant cleaning tool 1 or a dental floss or tape is minimal. The risk for triggering a foreign body response such as e.g. an inflammation or an allergic reaction is thus decreased.

Furthermore, a relatively rapid debridement procedure of surfaces, which are otherwise hard to clean and/or hard to reach by hand instrumentation, may be performed by means of the debridement and/or implant cleaning tool, such as a debridement and/or implant cleaning tool 1 or a dental floss or tape. Rapid treatment ensures a better treatment outcome. As mentioned above, it is a well-known fact that the morbidity and frequency of adverse effects, such as e.g. post-surgery effects, are directly related to, and often proportional to, the time used for the debridement of surgically exposed hard tissue surfaces. Thus, rapid debridement treatment ensures a better total treatment outcome.

A debridement and/or implant cleaning tool, such as a debridement and/or implant cleaning tool 1 or a dental floss or tape may also be used for the cleaning and/or debridement of soft tissues. Examples of soft tissues to be treated with a debridement and/or implant cleaning tool, such as a debridement and/or implant cleaning tool 1 or a dental floss or tape include, but are not limited to, keratinized or nonkeratinized gingival tissue, connective tissue, periodontal ligament, epithelium etc.

A debridement and/or implant cleaning tool, such as a debridement and/or implant cleaning tool 1 or a dental floss or tape may also be used for cleaning of implants, such as dental, orthopedic and/or vascular implants. Such cleaning may take place in vivo or in vitro. The implant may thus be cleaned by the debridement and/or implant cleaning tool, such as a debridement and/or implant cleaning tool 1 or a dental floss or tape when positioned in a body or when outside the body before its insertion into a body or after removal from its site in a body and before reposition therein. The debridement and/or implant cleaning tool, such as a debridement and/or implant cleaning tool 1 or a dental floss or tape may be used both for cleaning implants having relatively hard surfaces, such as e.g. medical and dental implants of steel, and titanium and implants having delicate surface structure, such as e.g. implants of titanium, a titanium alloy, zirconium or a zirconium alloy.

By utilizing the debridement and/or implant cleaning tool, such as a debridement and/or implant cleaning tool 1 or a dental floss or tape for cleaning the surface of an implant, the risk of formation of scratches on the implant, constituting bacteria adherence sites, is reduced. Thus, the risk of infection or re-infection in the tissue surrounding the implant is reduced.

The debridement and/or implant cleaning tool, such as a debridement and/or implant cleaning tool 1 or a dental floss or tape may e.g. be utilized during surgery for cleaning of the surface of an implant, such as a metallic implant or an implant having a metal containing surface, after infection and/or bone resorption. Thus, it may be utilized for removing e.g. bacterial biofilm, cement remnants, debris, calculus and/or fibrous tissue from the surface of an implant.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention will be further described in the following examples, which do not limit the scope of the invention described in the claims.

EXPERIMENTAL SECTION

Example 1

An injection moulded debridement tool for cleaning of exposed dental implant surfaces according to FIG. 1A was produced using injection moulding with a mixture of ultra-pure, pre-dried (less than 0.003% humidity), 85 wt % poly(L-lactide) (LPLA) and 10 wt % poly(DL-lactide) (DL-PLA) and 5 wt % PGA (all from Polysciences GmbH, Eppelheim, Germany). The mixture of polymers were melted at 180 degrees Celsius and injected into a pre-made form under pressure. The stem, made of nitinol attached to a hand piece connector made of surgical steel and welded in place, was present in the casting form so that the polymer working end of the debridement tool is casted directly around the stem. After injection the form with the injected material in place, was cooled down to room temperature, and the instrument, now consisting of a nitinol stem with a biodegradable working end attached, was removed from the cast. The device was then packaged in a gas-tight container for sterilization and storage before clinical use.

Example 2

An injection moulded debridement tool for cleaning of exposed dental implant surfaces according to FIG. 1A was produced using injection moulding with a mixture of ultra-pure, pre-dried (less than 0.003% humidity), 85 wt % poly(L-lactide) (LPLA) and 15 wt % poly(DL-lactide) (DL-PLA) (all from Polysciences GmbH, Eppelheim, Germany). The mixture of polymers were melted at 180 degrees Celsius and injected into a pre-made form under pressure. The stem, made of nitinol attached to a hand piece connector made of surgical steel and welded in place, was present in the casting form so that the polymer working end of the debridement tool is casted directly around the stem. After injection the form with the injected material in place, was cooled down to room temperature, and the instrument, now consisting of a nitinol stem with a biodegradable working end attached, was removed from the cast. The device was then packaged in a gas-tight container for sterilization and storage before clinical use.

Example 3

An injection moulded debridement tool for cleaning of exposed dental implant surfaces according to FIG. 1A was produced using injection moulding with a mixture of ultra-pure, pre-dried (less than 0.003% humidity), 58 wt % poly(L-lactide) (LPLA) and 42 wt % PGA (all from Polysciences GmbH, Eppelheim, Germany). The mixture of polymers were melted at 170 degrees Celsius and injected into a pre-made form under pressure. The stem, made of PVDF attached to a hand piece connector made of surgical steel and glued and press-fitted in place, was present in the casting form so that the polymer working end of the debridement tool is casted directly around the stem. After injection the form with the injected material in place, was cooled down to room temperature, and the instrument, now consisting of a nitinol stem with a biodegradable working end attached, was removed from the cast. The device was then packaged in a gas-tight container for sterilization and storage before clinical use.

Example 4

Figure 4:
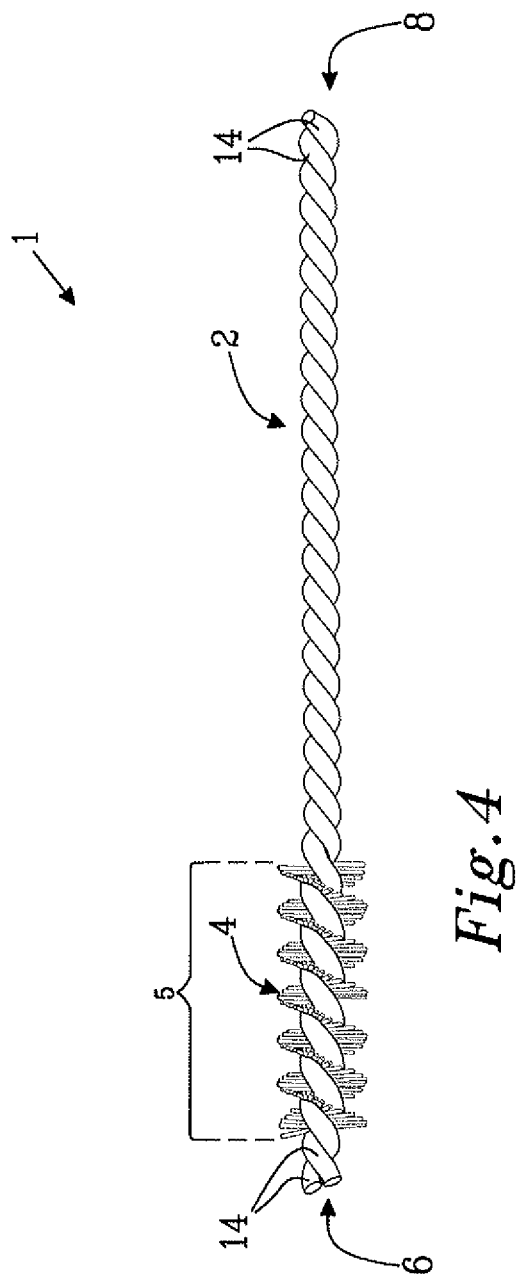
FIG. 4. Exemplary design of a debridement and/or implant cleaning tool 1 in the form of a twisted-in-wire brush.
Figure 5:
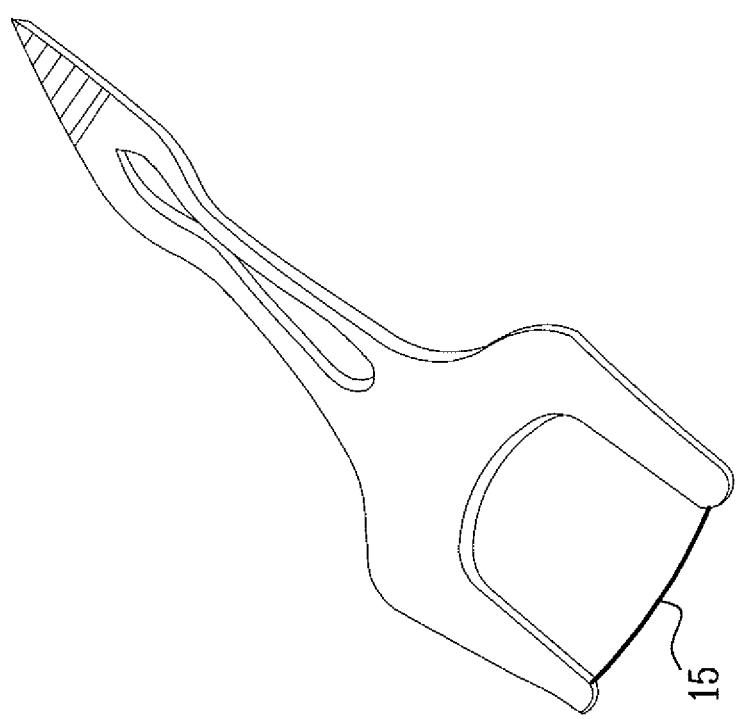
FIG. 5. Fig. A) Example of dental tape (a flat filament) inserted in floss holder. The Filament 15 can also be regular floss ("a round thread or yarn"). Filament 15 may be either permanently connected (fused) to the floss holder or separate and attached to the holder before use.

A twisted in wire debridement tool for cleaning of exposed dental implant surfaces according to FIG. 4 was produced using pre-made bristles made of poly(eta-caprolactone) (PCL) (melting point 64 degrees Celsius) (Polysciences GmbH, Eppelheim, Germany). The stem, made of cp grade 2 titanium wires, were twisted with the bristles placed in-wire at the working end. The twist wire stem was then attached to a hand piece connector made of surgical steel and welded in place. The instrument, now consisting of a twisted stem of titanium with a biodegradable working end was then packaged in a gas-tight container for sterilization and storage before clinical use.

Example 5

Figure 6:
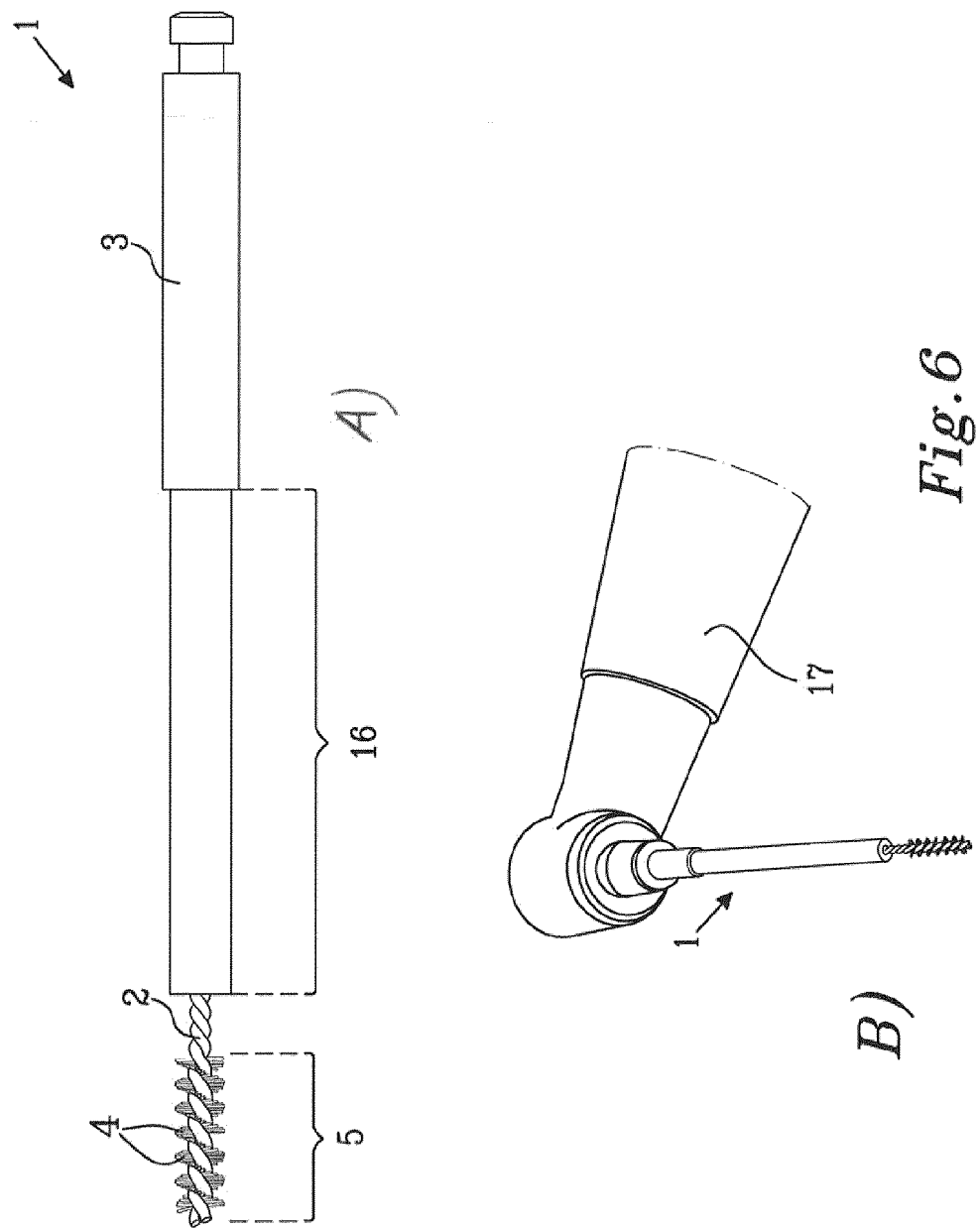
FIG. 6.

Treatment of Peri-Implant Mucositis with a Rotating Chitosan Brush a Case Report This case report describes the clinical use of a debridement and/or implant cleaning tool having means for cleaning 4 in the form of bristles made of chitosan (chitosan from Medovent GmbH, Mainz, Germany) for treatment of peri-implant mucositis. The brush was a debridement and/or implant cleaning tool 1 comprising an elongated base member 2 and means for cleaning 4 in a cleaning section 5 at a first end 6 of said base member 2 as disclosed herein. The base member 2 between the cleaning section 5 and the insert 3 (not shown) was coated with a protective cover 16. The brush used in this example is shown in FIG. 6. The protective coating of the brush used in this example was a 16 mm long nylon tube.

A 65-years old male patient presented with some clinical signs of oedematous and erythematous mucosa palataly of an implant seated posteriorly in the upper left quadrant. (Regio tooth 26, FDA). At peri-implant probing using a standard Michigan-0 probe a 5 mm mesial pocket was recorded. Bleeding on Probing was positive. Radiographic examination disclosed no signs of increase in approximal bone loss. Patient reported no subjective symptoms (e.g., pain).

A prototype of a chitosan brush (FIG. 6 A) attached to a motor-driven unit 17 in the form of a dental implant handpiece (FIG. 6 B) was used to debride the peri-implant pocket and implant surface. The chitosan brush had the design of a debridement and/or implant cleaning tool 1 with a) working end including the means for cleaning 4 in a cleaning section 5 of 2 mm in diameter and 8 mm in length with chitosan fibers 0.13 mm in diameter, double strand twisted in-wire of 0.3 mm medical grade stainless steel and b) 16 mm nylon tube 16 covering the metal elongated base member 2, and the tube inserted in to c) a stainless steel dental implant handpiece insert.

Figure 7:
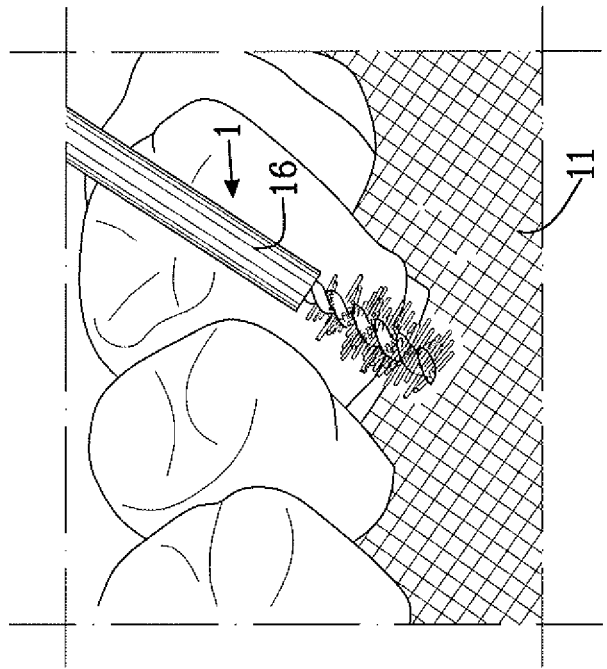
FIG. 7: Clinical treatment a dental implant mucosal crevice with mucositis. The chitosan brush 1 of Example 5 and depictured in FIG. 6 was used in a dental hand piece at 600 R.P.M. The mucosa is denoted 11.

Debridement was executed at 600 R.P.M. with a duration of 2 minutes and with saline irrigation (an illustration of this debridement is depictured in FIG. 7).

The brush penetrated well down in the mucosal crevice and the flexibility of the brush stem made it easy to access the approximal parts of the pocket. The crevice was rinsed with spurious amounts of sterile saline after finished debridement. The patient reported only minimal pain. After 2 weeks of healing the patient was controlled and presented with reduced signs of inflammation and no adverse effects from the therapy.

Figure 8:
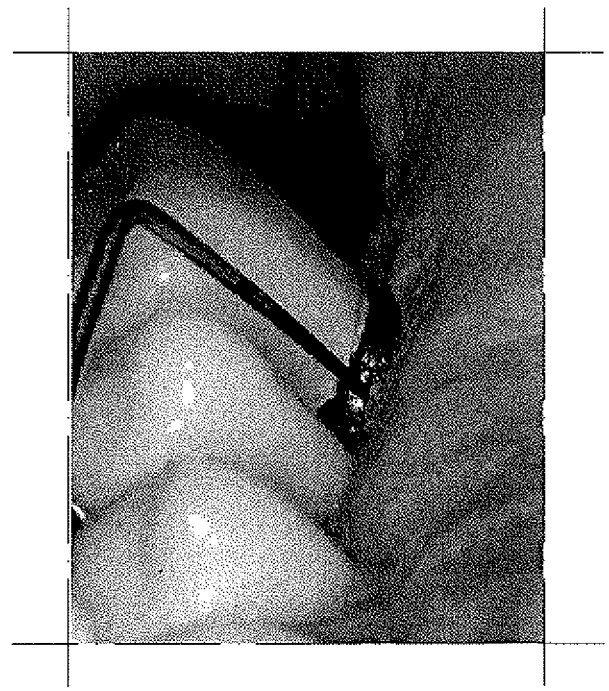
FIG. 8: Clinical situation at 4 weeks in Example 5. No signs of inflammation. Pocket depth 2 mm.

A second re-evaluation was performed 4 weeks after the therapy. The patient reported no subjective symptoms and the peri-implant mucosa now appeared completely healthy with no signs of oedema or erythema. The peri-implant crevice did not bleed on probing and the pocket depth was reduced from initially 5 mm to now 2 mm which indicates a healthy situation. See FIG. 8.

The invention claimed is:
1. A debridement and/or implant cleaning tool comprising an insert for a rotating, oscillating or ultrasonic handpiece, an elongated base member, and a cleaning section, wherein
   the insert comprises a metallic material;
   the base member connects the insert to the cleaning section and comprises a polymer; and
   the cleaning section comprises two or more wires being twisted with each other, and means for cleaning in the form of bristles inserted in between the twisted wires, the bristles comprising chitosan, wherein the diameter of the bristles is from about 0.05 mm to about 1 mm and the length of the bristles is from about 0.5 mm to about 5 mm.

2. A debridement and/or implant cleaning tool according to claim 1, wherein the means for cleaning further comprises a microbe growth inhibiting and/or microbe killing substance.

3. A debridement and/or implant cleaning tool according to claim 2, wherein said microbe growth inhibiting and/or microbe killing substance comprises an antibiotic or chlorhexidine.

4. A debridement and/or implant cleaning tool according to claim 1, wherein the polymer is a bioresorbable polymer.

5. A debridement and/or implant cleaning tool according to claim 4, wherein said means for cleaning and said base member are made of the same bioresorbable polymer(s).

6. A debridement and/or implant cleaning tool according to claim 1, wherein said polymer comprises a plastic material selected from the group consisting of nylon, polyethylene, vinyl, poly(methyl methacrylate), polyvinyl chloride, polyvinylidene fluoride, polytetrafluoroethylene, and polyvinyl fluoride.

7. A debridement and/or implant cleaning tool according to claim 1 wherein the means for cleaning are extended over the length of the cleaning section, so as to form a cylindrical, spherical, hour-glass shaped or tapered shape of the cleaning section.

8. A debridement and/or implant cleaning tool according to claim 1, wherein the diameter of the bristles is from about 0.05-0.5 mm.

9. A debridement and/or implant cleaning tool according to claim 1, wherein the diameter of the cleaning section is between about 0.5 and 5 mm.

10. A debridement and/or implant cleaning tool according to claim 1, wherein the cleaning section is about 5-12 mm long.

11. A debridement and/or implant cleaning tool according to claim 1, wherein the length of the debridement and/or implant cleaning tool, including both the base member and the cleaning section, is about 15-300 mm.

12. A dental debridement and/or dental implant cleaning tool according to claim 1, wherein the means for cleaning comprises a microbe growth inhibiting and/or microbe killing substance.

13. A dental debridement and/or dental implant cleaning tool according to claim 12, wherein the microbe growth inhibiting and/or microbe killing substance is an antibiotic or chlorhexidine.

14. A debridement and/or implant cleaning tool according to claim 1, wherein said rotating, oscillating or ultrasonic handpiece is a dental handpiece.

15. A debridement and/or implant cleaning tool according to claim 14, wherein the handpiece is a contra-angle hand piece.

16. An in vivo procedure for debriding and/or cleaning the surface of a dental tissue, a periodontal tissue, and/or a dental implant comprising the steps of:
 a) surgically exposing the surface to be treated;
 b) removing inflamed soft tissue;
 c) debriding and/or cleaning the surface with a debridement and/or implant cleaning tool according to claim 1,
 d) applying regenerative treatment as needed;
 e) replacing soft tissue; and
 f) suturing for good primary closure and wound stability.

17. The method of claim 16, wherein the tissue surface to be treated is associated with a condition selected from the group consisting of periimplantitis, periodontitis, furcation defects, apical granulomas, apical cysts, bone cysts, bone tumors, bone granulomas, bone cancers, extraction sockets, alveolitis sicca, apicectomy defects, localized osteomyelitis, trauma induced effects, resection or revision of implants, resection or revision of fractures, and removal of temporary bone implants.

18. A non-surgical in vivo procedure for debriding and/or cleaning the surface of a dental tissue, a periodontal tissue, and/or a dental implant comprising the steps of:
 a) removing supragingival plaque and debris to gain direct access to a periimplant sulcus and/or periimplant pocket;
 b) debriding and/or cleaning the surface by means of a debridement and/or implant cleaning tool according to claim 1; and
 c) applying regenerative treatment as needed.

19. The method of claim 18, wherein the surface to be cleaned is associated with a condition selected from the group consisting of periimplantitis, periodontitis, furcation defects, apical granulomas, apical cysts, bone cysts, bone tumors, bone granulomas, bone cancers, extraction sockets, alveolitis sicca, apicectomy defects, localized osteomyelitis, trauma induced effects, resection or revision of implants, resection or revision of fractures, and removal of temporary bone implants.

20. A method for debriding and/or cleaning a the surface of a dental tissue, a periodontal tissue, and/or a dental implant comprising the steps of placing a debridement and/or implant cleaning tool according to claim 1 against the surface to be debrided and/or cleaned and moving said debridement and/or implant cleaning tool thereover.

21. The method of claim 20, wherein the surface to be debrided and/or cleaned is associated with a condition selected from the group consisting of periimplantitis, periodontitis, furcation defects, apical granulomas, apical cysts, bone cysts, bone tumors, bone granulomas, bone cancers, extraction sockets, alveolitis sicca, apicectomy defects, localized osteomyelitis, trauma induced effects, resection or revision of implants, resection or revision of fractures, and removal of temporary bone implants.

* * * * *